United States Patent
Wilson et al.

(10) Patent No.: US 12,376,848 B2
(45) Date of Patent: Aug. 5, 2025

(54) AUTOMATED ROTATION OF A NEEDLE IN A COMPUTER-ASSISTED SYSTEM

(71) Applicant: INTUITIVE SURGICAL OPERATIONS, INC., Sunnyvale, CA (US)

(72) Inventors: Andrew D. Wilson, Hamden, CT (US); Gabriel F. Brisson, Livermore, CA (US); Robert C. Reid, Fairfield, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 272 days.

(21) Appl. No.: 17/918,865

(22) PCT Filed: Apr. 13, 2021

(86) PCT No.: PCT/US2021/027134
§ 371 (c)(1),
(2) Date: Oct. 13, 2022

(87) PCT Pub. No.: WO2021/211617
PCT Pub. Date: Oct. 21, 2021

(65) Prior Publication Data
US 2023/0190262 A1 Jun. 22, 2023

Related U.S. Application Data

(60) Provisional application No. 63/009,961, filed on Apr. 14, 2020.

(51) Int. Cl.
*A61B 17/04* (2006.01)
*A61B 17/00* (2006.01)
(Continued)

(52) U.S. Cl.
CPC .......... *A61B 17/0482* (2013.01); *A61B 34/71* (2016.02); *A61B 2017/00137* (2013.01);
(Continued)

(58) Field of Classification Search
CPC ................ A61B 17/0482; A61B 34/71; A61B 2017/00137; A61B 2017/00973; A61B 2017/0608
See application file for complete search history.

(56) References Cited

U.S. PATENT DOCUMENTS

| 8,123,764 B2 | 2/2012 | Meade et al. |
| 9,724,087 B2 | 8/2017 | Berry |

(Continued)

FOREIGN PATENT DOCUMENTS

CN 108498126 A 9/2018

OTHER PUBLICATIONS

International Search Report and Written Opinion for Application No. PCT/US2021/027134, mailed Jul. 29, 2021, 10 pages.

(Continued)

*Primary Examiner* — Tan-Uyen T Ho
*Assistant Examiner* — Khoa Tan Le
(74) *Attorney, Agent, or Firm* — Artegis Law Group, LLC

(57) ABSTRACT

Techniques for automated rotation of a needle in a computer-assisted system include an end effector having a drive mechanism configured to be coupled to a curved needle and configured to rotationally actuate the curved needle along an arcuate path and a control unit coupled to the drive mechanism. The control unit is configured to, in response to receiving a first input, cause the drive mechanism to rotationally actuate the curved needle by a first preset rotation amount along the arcuate path, and, in response to receiving a second input, cause the drive mechanism to rotationally (Continued)

actuate the curved needle by a second preset rotation amount along the arcuate path.

20 Claims, 9 Drawing Sheets

(51) Int. Cl.
     *A61B 17/06*       (2006.01)
     *A61B 34/00*       (2016.01)

(52) U.S. Cl.
     CPC ............... *A61B 2017/00973* (2013.01); *A61B 2017/0608* (2013.01)

(56) References Cited

U.S. PATENT DOCUMENTS

| | | |
|---|---|---|
| 10,470,758 B2 * | 11/2019 | Mumaw ............ A61B 17/06133 |
| 2006/0292917 A1 | 12/2006 | Miyamoto et al. |
| 2013/0282029 A1 | 10/2013 | Skinlo et al. |
| 2016/0367243 A1 * | 12/2016 | Martin ............. A61B 17/06133 |
| 2017/0150961 A1 * | 6/2017 | Marczyk ............ A61B 17/0625 |
| 2019/0206565 A1 | 7/2019 | Shelton, IV |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

← Distal        Proximal →

AUTOMATED ROTATION OF A NEEDLE IN A COMPUTER-ASSISTED SYSTEM

CROSS-REFERENCES TO RELATED APPLICATIONS

The present application is a U.S. National Stage patent application of International Patent Application No. PCT/US2021/027134, filed Apr. 13, 2021, the benefit of which is claimed, and claims priority to U.S. Provisional Patent Application No. 63/009,961 filed Apr. 14, 2020, each of which is hereby incorporated herein by reference in its entirety.

TECHNICAL FIELD

The present disclosure relates generally to operation of devices with actuatable instruments and more particularly to automated rotation of a needle in a computer-assisted system.

BACKGROUND

Compared to conventional open site procedures, minimally invasive procedures may be performed with suitably configured devices that may be introduced into a workspace through a small opening, such as a port, an orifice, and/or an incision site. In some medical examples, minimally-invasive procedures help reduce trauma and disability, help reduce a chance of infection, and/or improve recovery time. Because minimally invasive procedures involve the insertion and manipulation of instruments through ports, small incisions, and/or natural orifices, the work site within the workspace is not as accessible as in open site procedures. As a result, manipulating such instruments may be awkward, particularly when the operator performs complicated tasks like stitching a material or stitching a suture. In addition, human hands typically have some minimal amount of tremor, which may further increase the difficulty of certain minimally invasive tasks.

To address the limitations of minimally invasive procedures, computer-assisted devices have been developed. During procedures with a computer-assisted device, the dexterity of the operator when utilizing the instruments inserted into the workspace is enhanced. Instruments with end effectors for performing various tasks include forceps, needle drivers, clip appliers, retractors, cautery instruments, suturing devices, and/or the like, which can be actuated to grasp, sever, cauterize, suture, and/or otherwise precisely manipulate material, such as tissue and/or other objects. However, even with the improved dexterity afforded by such computer-assisted devices, the stitching of material (e.g., tissue) and setting of the knots is generally a difficult and time-consuming process, due to the complicated motions involved and the lack of space that is available for movement of the end effectors in the workspace.

Accordingly, improved methods and systems for stitching a material during minimally invasive procedures are desirable.

SUMMARY

Consistent with some embodiments, a computer-assisted device includes an end effector having a drive mechanism configured to be coupled to a curved needle and configured to rotationally actuate the curved needle along an arcuate path and a control unit coupled to the drive mechanism. The control unit is configured to, in response to receiving a first input, cause the drive mechanism to rotationally actuate the curved needle by a first preset rotation amount along the arcuate path, and, in response to receiving a second input, cause the drive mechanism to rotationally actuate the curved needle by a second preset rotation amount along the arcuate path.

Consistent with some embodiments, a computer-assisted device includes an end effector having a drive mechanism configured to be coupled to a curved needle and configured to rotationally actuate the curved needle along an arcuate path and a control unit coupled to the drive mechanism. The control unit is configured to receive an operator input signal, based on a mapping of the operator input signal to a rotational arc amount of the curved needle, determine an arc of rotation for the curved needle along an arcuate path corresponding to the operator input signal, and cause the drive mechanism to rotationally actuate the curved needle through the arc of rotation along the arcuate path.

Consistent with some embodiments, in a computer-assisted device that includes an end effector, a method includes, in response to receiving a first input, causing a drive mechanism of the end effector to rotationally actuate a curved needle coupled to the drive mechanism by a first preset rotation amount along an arcuate path, and, in response to receiving a second input, causing the drive mechanism to rotationally actuate the curved needle by a second preset rotation amount along the arcuate path.

Consistent with some embodiments, in a computer-assisted device that includes an end effector having a drive mechanism configured to be coupled to a curved needle and configured to rotationally actuate the curved needle along an arcuate path, a method includes receiving an operator input signal, based on a mapping of the operator input signal to a rotational arc amount of the curved needle, determining an arc of rotation for the curved needle along the arcuate path corresponding to the operator input signal, and causing the drive mechanism to rotationally actuate the curved needle through the arc of rotation along the arcuate path.

Consistent with some embodiments, a non-transitory machine-readable medium including a plurality of machine-readable instructions which when executed by one or more processors are adapted to cause the one or more processors to perform any of the methods described herein.

Figure 1:
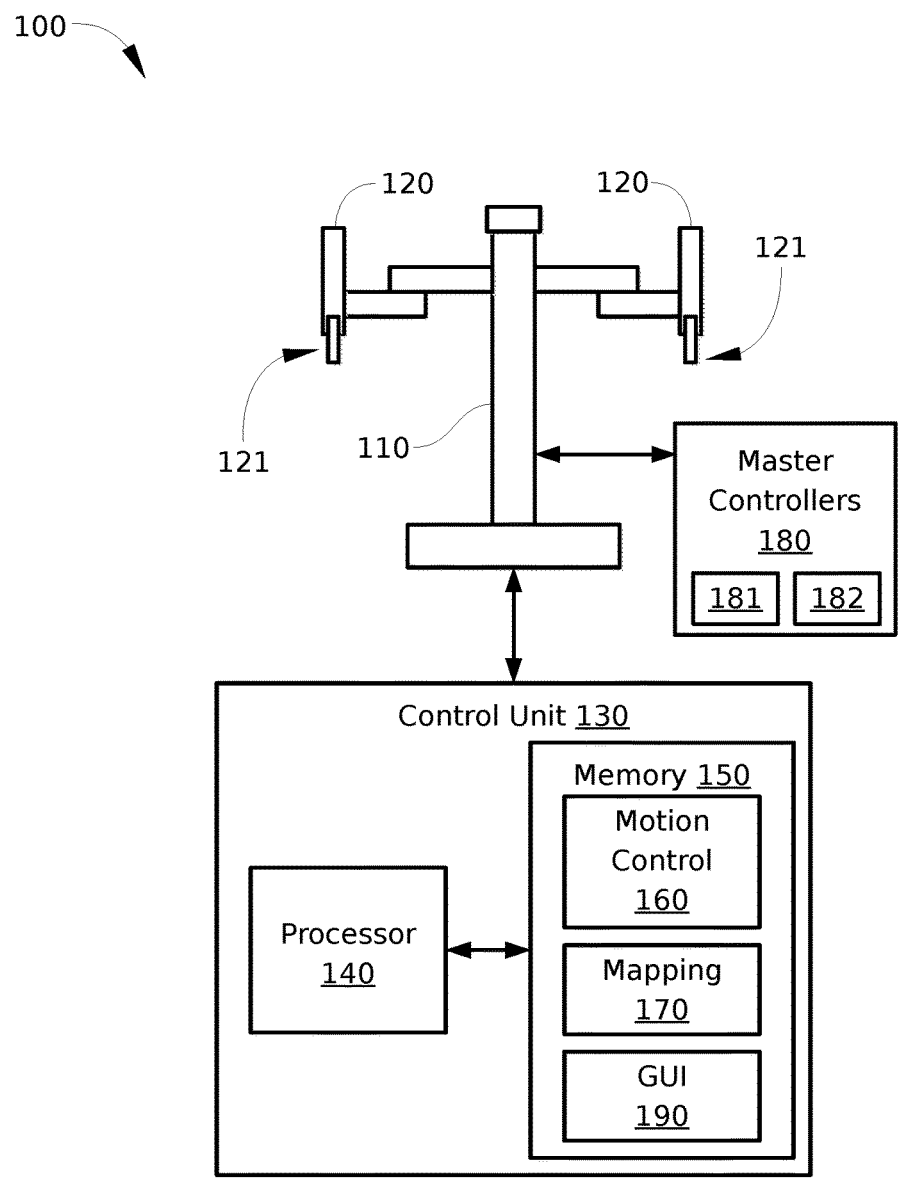
FIG. 1 is a simplified diagram of a computer-assisted system according to some embodiments.

In the figures, elements having the same designations have the same or similar functions.

DETAILED DESCRIPTION

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the term "below," for example, can encompass both positions and orientations of above and below. A device may be otherwise oriented (e.g., rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw, angle-axis, rotation matrix, quaternion representation, and/or the like). As used herein, the term "pose" refers to the six degree of freedom (DOF) spatial position and orientation of an element or a portion of an element. As used herein, the term "shape" refers to a set of positions and/or orientations measured along an element. As used herein, and for a computer-assisted device with repositionable arms, the term "proximal" refers to a direction toward the base of the computer-assisted device along its kinematic chain and the term "distal" refers to a direction away from the base along the kinematic chain.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on da Vinci® Surgical Systems are merely examples and are not to be considered as limiting the scope of the inventive aspects disclosed herein. In some embodiments, the instruments, systems, and methods described herein may be suitable for use in, for example, surgical, teleoperated surgical, diagnostic, therapeutic, or biopsy procedures. While some embodiments are provided herein with respect to such procedures, any reference to medical or surgical instruments and medical or surgical methods is intended as non-limiting. Thus, the instruments, systems, and methods described herein may be used for humans, animals, portions of human or animal anatomy, non-surgical diagnosis, as well as for industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

FIG. 1 is a simplified diagram of a computer-assisted system 100 according to some embodiments. As shown in FIG. 1, computer-assisted system 100 includes a device 110 with one or more movable or repositionable arms 120. Each of the one or more repositionable arms 120 may support and drive one or more end effectors 121. In some examples, device 110 may be a computer-assisted surgical device. The one or more repositionable arms 120 each provide support for and drive surgical instruments, imaging devices, and/or the like. The end effectors 121 may be located at a distal end portion of the surgical instruments. In some embodiments, computer-assisted surgical devices with other configurations, fewer or more articulated arms, and/or the like may be used with computer-assisted system 100.

In some embodiments, the device 110 may be mounted near or adjacent an operating or surgical table, or the device 110 may be mounted directly to the table, or to a rail coupled to the table, or integrally part of the table structure. In some embodiments, the device 110 may be a movable cart (e.g., a patient-side cart). The movable cart may be separate from and spaced from the table in the operating room and may be independently movable relative to the table. In some embodiments, the movable cart may be docked or attached to the table. In some embodiments, the device 110 may be mounted to a ceiling, floor, and/or wall of the operating room. In some embodiments having a plurality of devices 110, each device may be mounted to any structure or in any manner as described above. For example, one device 110 may be mounted to a surgical table and another device 110 may be mounted to a ceiling.

Device 110 may further be coupled to an operator workstation (not shown), which may include one or more master controls 180 for selectively operating device 110, the one or more repositionable arms 120, and/or the end effectors. Master controls 180 are input devices that enable an operator to manipulate end effectors 121 and, in some embodiments, repositionable arms 120. Specifically, as the operator performs a procedure by manipulating one or more master controls 180, control unit 130 causes one or more slave manipulators to manipulate a respective repositionable arm 120 and/or end effector 121. In some embodiments, the movements of master controls 180 the associated devices are scaled, which can facilitate performance of intricate procedures with greater ease than conventional open-site procedures. Master controls 180 may include one or more continuous motion input devices 181 and/or one or more digital input devices 182. In some embodiments, device 110, the operator workstation, and the control unit 130 may correspond to a da Vinci® Surgical System commercialized by Intuitive Surgical, Inc. of Sunnyvale, California.

The one or more continuous motion input devices 181 are configured to enable an operator to generate an input that varies along a continuum of values, for example, from 0% to 100% of a particular input range. As such, each of the one or more continuous motion input devices 181 can include any one or more of a variety of input devices, such as joysticks, gloves, trigger-guns, hand-operated controllers (grippers, sliders, knobs, rotary inputs, etc.) and/or the like. Alternatively or additionally, in some embodiments, one or more of the continuous motion input devices 181 may be configured to enable an operator to generate multiple inputs that each vary along a respective continuum of values. For example, in an embodiment, a particular continuous motion input device 181 includes a different continuous input generator for each degree of freedom of an end effector 121 that is currently associated with that particular continuous motion input device 181.

The one or more digital input devices 182 are configured to enable an operator to generate a digital or binary input. Thus, each of the one or more digital input devices 182 enables an operator to toggle between a first mode and a second mode, select and deselect a specific control option of device 110, etc. For example, in an embodiment, a first actuation of a particular digital input device 182 by an operator causes an energy delivery instrument included in an end effector 121 to be energized and a second actuation of the particular digital input device 182 by the operator causes the energy delivery instrument to be de-energized. Suitable examples of digital input devices 182 include a foot pedal, a hand- or foot-operated button, a switch, a lever, and/or the like.

Device 110 is coupled to a control unit 130 via an interface. The interface may include one or more cables, connectors, and/or buses, and may further include one or more networks (e.g., wired and/or wireless networks) with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), tensor processing units (TPUs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that may be used to support autonomous and/or semiautonomous control of device 110. Motion control application 160 may include one or more application programming interfaces (APIs) for receiving position, orientation, motion, and/or other sensor information from device 110, exchanging position, orientation, motion, and/or collision avoidance information with other control units regarding other devices, such as a surgical table and/or imaging device, and/or planning and/or assisting in the planning of motion for device 110, repositionable arms 120, and/or end effectors 121 of device 110. And although motion control application 160 is depicted as a software application, motion control application 160 may be implemented using hardware, firmware, software, and/or a combination thereof, any of which interact with or are otherwise executed by processor 140.

In some embodiments, memory 150 further includes a mapping 170 that maps values of a proportional input signal from a continuous motion input device 181 to a particular rotational arc amount (e.g., of a rotational drive mechanism in an end effector). Mapping 170 can include any technically feasible mapping of proportional input signals to rotational arc amounts.

For example, in an embodiment in which a continuous motion input device 181 includes a gripping controller, mapping 170 maps values of the proportional input signal from the gripping controller to corresponding values of rotational arc of a drive mechanism included in an end effector 121. In one such embodiment, a proportional input signal value corresponding to 0% gripping motion is mapped to 0 degrees of rotational arc, a proportional input signal value corresponding to 100% gripping motion is mapped to 180 degrees of rotational arc, and proportional input signal values corresponding to gripping motion between 0% and 100% gripping motion are distributively mapped to respective rotational arcs between 0 degrees and 180 degrees of rotational arc. In another embodiment, a proportional input signal value corresponding to 0% gripping motion is mapped to 0 degrees of rotational arc, a proportional input signal value corresponding to 100% gripping motion is mapped to 360 degrees of rotational arc, and proportional input signal values corresponding to gripping motion between 0% and 100% gripping motion are distributively mapped to respective rotational arcs between 0 degrees and 360 degrees of rotational arc. In some embodiments, the gripping motion of the gripping controller may be continuously movably between a fully open state (e.g., corresponding to 0% gripping motion) and a fully closed state (e.g., corresponding to 100% gripping motion), or vice versa. In some embodiments gripping motion may be distributively mapped from 0 degrees of rotational arc to less than 180 degrees of rotation arc at 100% gripping motion. In some embodiments the mapping of the fully opened and fully closed states may be reversed, for example, with the fully open state corresponding to 100% gripping motion and the fully closed state corresponding to 0% gripping motion. In some embodiments, the gripping motion may be constrained to be movable to an extent less than fully open and fully closed states.

Alternatively, in an embodiment in which a continuous motion input device 181 includes a rotary input device, such as a rotating knob, mapping 170 maps values of the proportional input signal from the rotary input device to corresponding values of rotational arc of a drive mechanism included in an end effector 121. In one such embodiment, a proportional input signal value has a 1:1 mapping between rotation of the rotary input device and rotational arc of the drive mechanism. Thus, in such an embodiment, 0% rotation of the rotary input device is mapped to a signal resulting in 0 degrees of rotational arc of the drive mechanism, while 100% (e.g., 360 degrees) rotation of the rotary input device is mapped to a signal resulting in a complete 360-degree rotation of the drive mechanism. In some embodiments, the rotary input device is configured to be continuously movable in one rotational direction only (e.g., clockwise), and in some embodiments the rotary input device is configured to be continuously movable in both the clockwise and the counterclockwise directions. In some embodiments, the rotary input device is configured with a hard stop limiting motion in one direction, such as the direction of rotation of the reciprocating drive mechanism. In some embodiments, the rotary input device is configured to provide feedback to the operator (e.g., haptic feedback), for example to indicate when a curved needle being driven by the drive mechanism is being commanded to certain positions, such as when the curved needle extends out of a housing of the end effector 121, or when the needle is fully retracted in such a housing, based on the rotational position of the drive mechanism.

In yet another embodiment, mapping 170 includes a first mapping of proportional input signal values of a first proportional input signal from a continuous motion input device 181 and a second mapping of proportional input signal values of a second proportional input signal from the same continuous motion input device 181, with the first mapping and the second mapping being mapped to corresponding values of rotational arc of a drive mechanism included in an end effector 121. In such an embodiment, the first proportional input signal from the continuous motion input device 181 may be generated by motion or actuation of the continuous input device 181 in a first direction and the second proportional input signal from the continuous motion input device 181 may be generated by motion or actuation of the continuous input device 181 in a second direction different from the first direction. Positions of the gripping controller while being closed (e.g., while gripping motion of the gripping controller is moved from an open state to a closed state) may correspond to proportional input signals distributed through a first preset rotational amount. In addition, positions of the gripping controller while being opened (e.g., while gripping motion of the gripping controller is moved from a closed state to an open state) may correspond to proportional input signals distributed through a second preset rotational amount. For example, in some embodiments in which the continuous input device 181 is a gripping controller, the first mapping may map proportional input signal values generated by the gripping controller while being closed. The first mapping may be mapped to respective rotational arcs between 0 degrees and 180 degrees of rotational arc of a drive mechanism included in an end effector 121. Similarly, the second mapping may map proportional input signal values generated by the gripping controller while being opened. In some embodiments, the drive mechanism may be configured to continuously reciprocate around 360 degrees of rotational arc. In such embodiments, the second mapping may be mapped to respective rotational arcs between 180 degrees and 360 degrees of rotational arc of the drive mechanism. Alternatively, the drive mechanism may be configured to reciprocate around less than 360 degrees of rotational arc. For example, the drive mechanism may be configured with 180 degrees of rotational arc, wherein the first mapping may be mapped to rotational arcs between 0 and 180 degrees of the drive mechanism and the second mapping may be mapped to respective rotational arcs between 180 degrees and 0 degrees of the drive mechanism (i.e., opposite to the mapping of the first mapping). In some embodiments, the drive mechanism may be configured with 180 degrees of rotational actuation. In such embodiments, the second mapping may be mapped to a reverse stroke of the drive mechanism, in which the drive mechanism returns from 180 degrees of rotation back to 0 degrees of rotation.

In some embodiments, memory 150 further includes a graphical user interface (GUI) 190 that facilitates operation of device 110, including repositionable arms 120 and/or end effectors 121. In some embodiments, GUI 190 presents one or more visual elements to an operator for interacting with device 110, such as icons, menus, graphical panels, graphical buttons, and/or the like. One embodiment of GUI 190 is described further below in conjunction with FIG. 8.

In some embodiments, computer-assisted system 100 may be found in an operating room and/or an interventional suite. And although FIG. 1 depicts computer-assisted system 100 with one device 110 having two repositionable arms 120, one of ordinary skill would understand that computer-assisted system 100 may include any number of devices with repositionable arms and/or end effectors 121 of similar and/or different design from device 110. In some examples, each of the devices may include fewer or more repositionable arms and/or end effectors 121.

According to various embodiments, one or more of end effectors 121 are configured to rotatably actuate a needle (such as a suturing needle) of a stitching or suturing device. An operator may control the rotational actuation of the needle by using a continuous motion of a continuous motion input device (such as continuous motion input device 181), by using a digital input (such as digital motion input device 182, for example, by depressing a button, a foot pedal, a lever, and/or the like), and/or any combination thereof. In one example, the continuous motion of the continuous motion input device is mapped to rotational motion of the needle relative to an axis of a needle track on the device (e.g., a curved needle track), so that a continuous change in the motion of the input device (e.g., a continuous change in a position of the input device) results in a corresponding rotational motion of the needle. In another example, actuation of the digital input results in autonomous rotational actuation of the needle. For example, depression of a foot pedal or a push of a button may cause the needle to autonomously rotate through a 180° or 360° arc. Thus, execution of a complete stitch can be commanded by an operator by appropriately positioning the needle near a target material to be stitched (such as tissue in a medical example) and then actuating the digital input (e.g., by depressing the foot pedal, pushing a button, etc.). This process allows for multiple complete stitches to be created quickly and accurately. Consequently, the large sequence of individual needle manipulations normally employed in creating a stitch may be simplified. Various embodiments of end effectors 121 are described below in conjunction with FIGS. 2-6.

In some embodiments, a curved needle may be coupled to a drive mechanism included in the end effector 121. The drive mechanism is configured to rotate the curved needle around a rotational arc, such as around a curved needle track. The drive mechanism may be controlled by an operator via manipulation of the continuous motion input device, the digital input, and/or any combination thereof.

Figure 2:
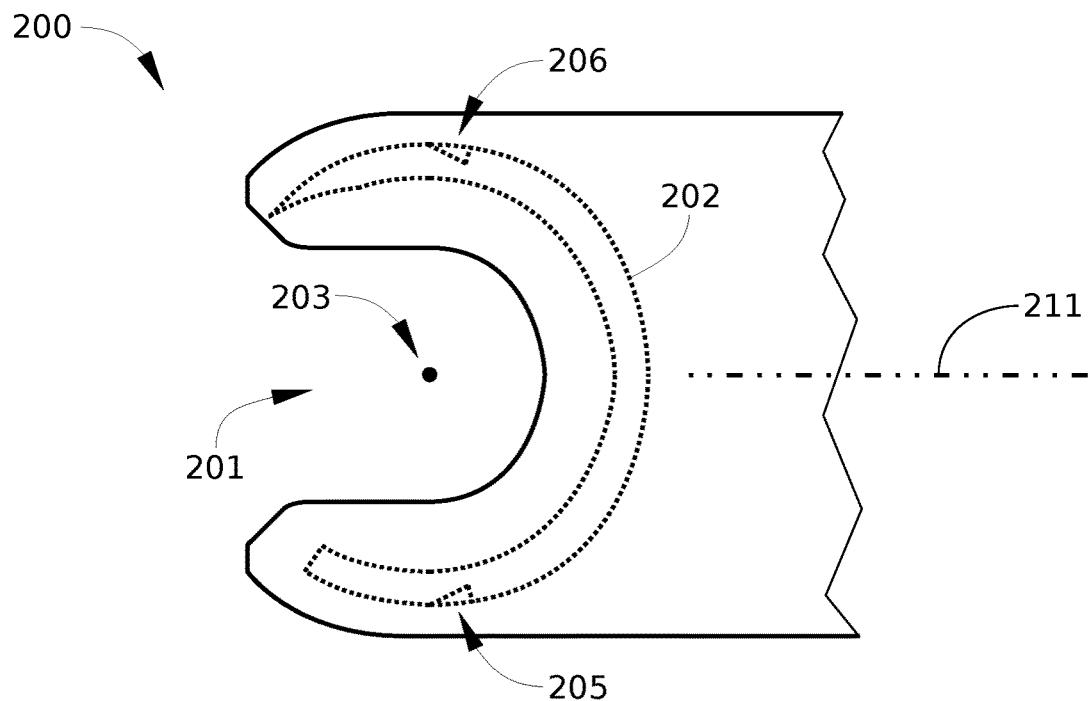
FIG. 2 is a schematic diagram of an end effector according to some embodiments.

FIG. 2 is a schematic diagram of an end effector 200 of an instrument configured according to some embodiments. End effector 200 is a portion of a stitching device configured for performing minimally invasive stitching and can be employed as an end effector 121 of FIG. 1. End effector 200 is disposed near a distal end of an instrument shaft and includes a stitching aperture 201, a curved needle 202 (which is hidden in FIG. 2 and shown in dashed lines), and a drive mechanism (not shown). As described in further detail below, the curved needle 202 may move along an arcuate needle path. In some embodiments, the curved needle 202 moves along an arcuate needle track within end effector 200 about an axis 203. The arcuate needle track defines an arcuate needle path along which curved needle 202 moves. The drive mechanism is configured to be coupled to curved needle 202 and to rotationally actuate curved needle 202 around the arcuate needle track along an arcuate path. In some embodiments, curved needle 202 is formed as a portion of a circle, however, the curved needle 202 may have other shapes. In some embodiments, axis 203 includes or passes through a center point of a circle defined by the arcuate needle track and, in some embodiments, axis 203 may be located within stitching aperture 201. Axis 203 is oriented to be substantially perpendicular to a longitudinal axis 211 of end effector 200, and therefore is shown as a point in FIG. 2.

In operation, stitching material or thread (not shown) is connected to curved needle 202, for example via an attachment opening or other feature, and the drive mechanism of end effector 200 drives curved needle 202 in a curved path about axis 203. In some embodiments, the drive mechanism drives curved needle 202 around the arcuate needle track via two drive notches 205 and 206 that are each formed on an outer face of curved needle 202, for example at about 180 degrees apart. Drive notch 205 may be located near a trailing end of curved needle 202 and drive notch 206 may be located near a leading end of curved needle 202. The leading end of the curved needle 202 may have a sharpened tip. Embodiments of drive mechanisms are described in greater detail below in conjunction with FIGS. 3-6.

Figure 3:
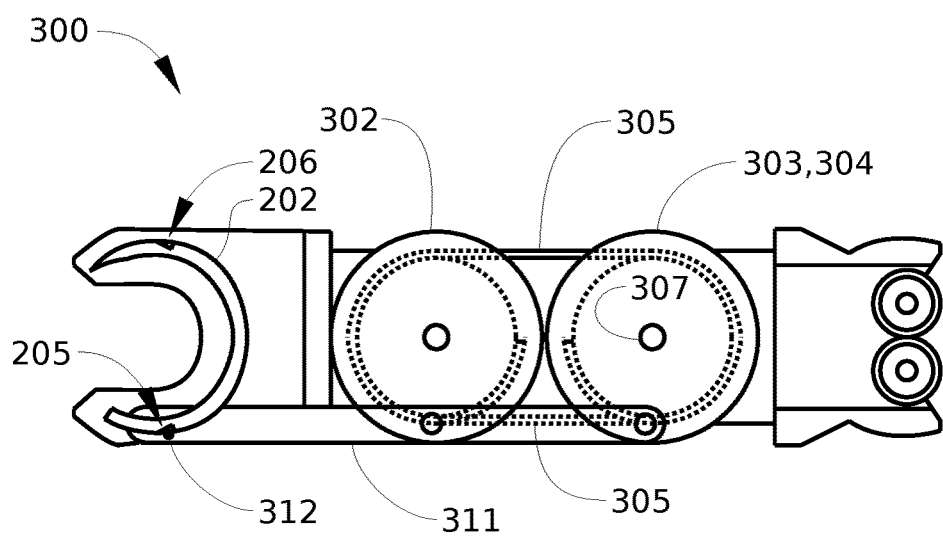
FIG. 3 shows elements of a drive mechanism of an end effector according to some embodiments.

FIG. 3 shows elements of a drive mechanism 300 of end effector 200, configured according to some embodiments. A housing of drive mechanism 300 is omitted in FIG. 3 for clarity. In the embodiment illustrated in FIG. 3, drive mechanism 300 includes a follower pulley 302, a drive pulley 304, and a drive pulley 303, which is hidden by drive pulley 304 in FIG. 3. As shown, follower pulley 302 and drive pulley 304 are rotationally coupled to each other via connectors 305, which partially wrap around follower pulley 302 and drive pulley 304. The connectors 305 may be belts, cables, and the like. Drive pulley 303 is coupled to and rotates about the same axis 307 as drive pulley 304. In alternate embodiments, follower pulley 302 may be coupled to drive pulley 304 via connectors 305. In operation, follower pulley 302, drive pulley 304, and drive pulley 303 are configured to rotate in sync together, for example over a rotational arc of about 190 degrees. The synchronized rotation of follower pulley 302 and drive pulleys 303 and 304 causes an actuator arm 311 to rotationally drive curved needle 202. As described in further detail below, actuator arm 311 includes a pawl 312 that is configured to releasably engage drive notches 205 and 206 on curved needle 202 to drive curved needle 202 through a 360 arc of rotation. Pawl 312 engages drive notch 205 to drive the needle 202 through an approximate 180 degree arc, releases from drive notch 205, and then engages drive notch 206 to drive needle 202 through another approximate 180 degree arc.

Figure 4:
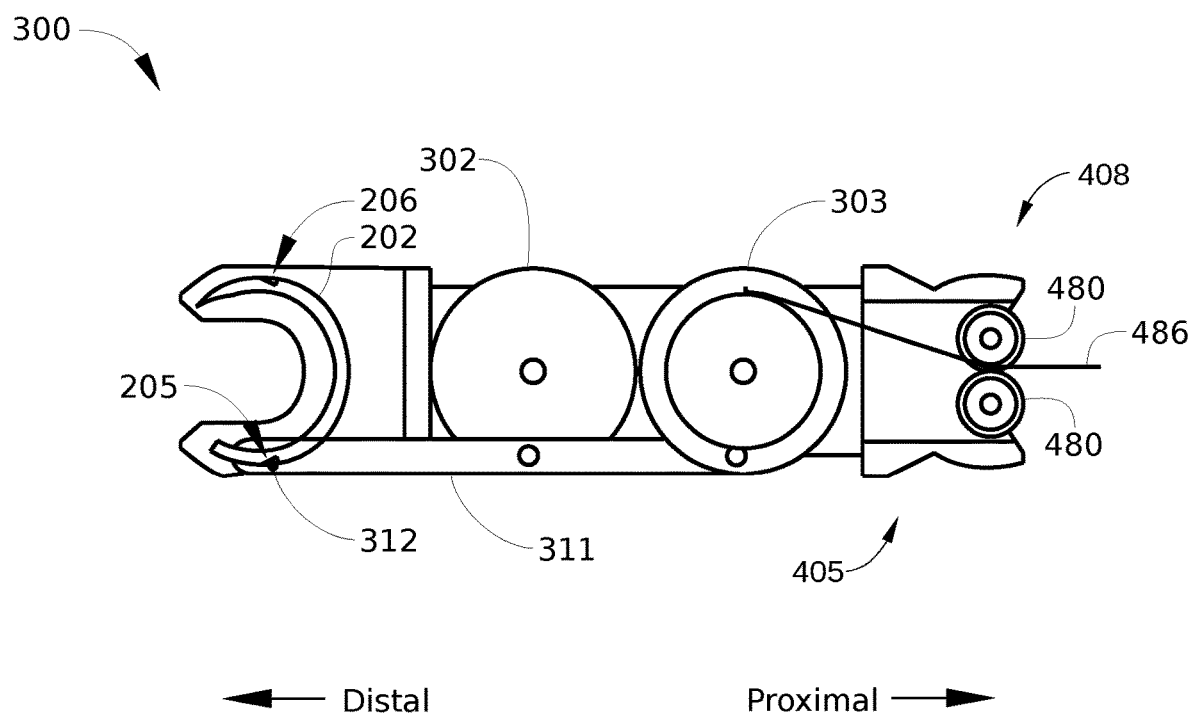
FIGS. 4 and 5 show further elements of the drive mechanism of FIG. 3 according to some embodiments.
Figure 5:
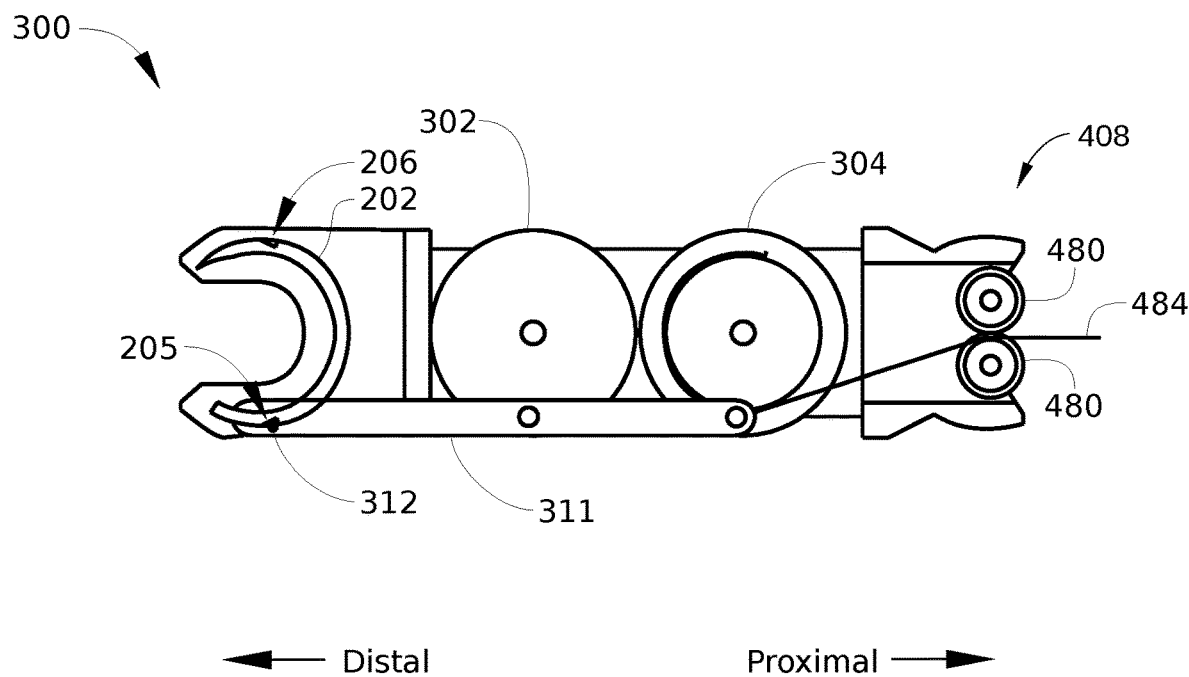

FIGS. 4 and 5 show further elements of drive mechanism 300 of end effector 200, configured according to some embodiments. Drive mechanism 300 further includes cables 484 and 486, which may be made from stainless steel or any other suitable material. Cable 484 (shown in FIG. 5) is connected to drive pulley 304, and cable 486 (shown in FIG. 4) is connected to drive pulley 303. Connected at a proximal end 405 of drive mechanism 300 is a portion 408 that contains part of drive mechanism 300 that includes two idler pulleys 480 and cables 484 and 486. FIG. 4 shows drive mechanism 300 with drive pulley 303 in place (and drive pulley 304 hidden from view) and cable 486 running through idler pulleys 480 and wrapped around drive pulley 303. FIG. 5 shows drive mechanism 300 with drive pulley 303 removed and cable 484 running through idler pulleys 480 and wrapped around drive pulley 304. Cable 484 runs from drive pulley 303 through an instrument shaft connected to the proximal end of the end effector 200 to a suitable drive mechanism disposed in a proximal portion of instrument shaft.

The curved needle 202 is configured to be moved between a home position in which the needle 202 is retracted within a housing of the drive mechanism 300 and an engaged position in which the needle 202 extends from the housing and across aperture 201 to engage in tissue. In some embodiments, the engaged position may correspond to the curved needle rotating approximately 180 degrees relative to the home position. To drive curved needle 202, actuator arm 311 is configured to be moved along an arcuate path within the housing. In various examples, actuator arm 311 may be configured to move along an approximate 180 degree arc, an approximate 190 degree arc, etc. In some embodiments, actuator arm may move along an arcuate path between a needle-driving position corresponding to an approximate 6 o'clock rotational position (as shown in FIGS. 4-5) and a needle-ending position corresponding to an approximate 12 o'clock rotational position. The rotational positions are provided by way of example and various other rotational positions are possible for the needle-driving position and the needle-ending position.

In an example embodiment, the force to rotationally actuate curved needle 202 from the home position to the engaged position is provided by a cable-tensioning device (not shown) that is connected to cable 484. Thus, to rotationally actuate curved needle 202 from the home position (as shown in FIGS. 4 and 5) to the engaged position in which the needle 202 extends from the housing, an operator performs a suitable input action with an input device as described herein, and the cable-tensioning device that is connected to cable 484 causes drive pulley 304 to turn counterclockwise (relative to the orientations shown in FIGS. 4 and 5). The counterclockwise rotation of drive pulley 304 drives actuator arm 311 from the needle-driving position to the needle-ending position. The curved needle 202 is correspondingly moved through approximately 180 degrees of rotational arc via engagement of actuator arm 311 with drive notch 205 such that the curved needle 202 moves across aperture 201. Following the counterclockwise rotation of the actuator arm 311 from the needle-driving position to the needle-ending position to drive the curved needle 202, the actuator arm 311 is disengaged from the curved needle 202. The actuator arm 311 may then be returned to the needle-driving position without driving the curved needle 202. To rotationally actuate curved needle 202 from the engaged position to the home position, an operator performs a suitable input action with an input device as described herein, and the cable-tensioning device that is connected to cable 484 causes drive pulley 304 to again turn counterclockwise. In this instance, the counterclockwise rotation of drive pulley 304 drives actuator arm 311 from the needle-driving position to the needle-ending position to move curved needle 202 through approximately 180 degrees of rotational arc via engagement of actuator arm 311 with drive notch 206. The orientation of the curved needle 202 relative to the housing and the counterclockwise motion of the actuator arm 311 from the needle-driving position to the needle-ending position are by way of example only. In alternate embodiments, the orientation of the needle may be reversed, such that the needle and actuator arm 311 may move in a clockwise motion from the needle-driving position to the needle-ending position.

In an example embodiment, the force to move actuator arm 311 from the needle-ending position to the needle-driving position is provided by a cable-tensioning device (not shown) that is connected to cable 486. Thus, to rotationally return actuator arm 311 from the needle-ending position to the needle-driving position, an operator performs a suitable input action with an input device as described herein. In response, the cable-tensioning device that is connected to cable 486 causes drive pulley 303 to turn clockwise, through approximately 180 degrees. In this way, actuator arm 311 is returned to the needle-driving position, as shown in FIGS. 4 and 5.

In operation, a stitching cycle is completed in four steps. First, with the actuator arm 311 in the needle-driving position and pawl 312 engaged with drive notch 205 of curved needle 202, tension in cable 484 causes follower pulley 302, drive pulley 304, and drive pulley 303 to rotate counterclockwise for approximately 180 degrees to drive actuator arm 311 to the needle-ending position and drive curved needle 202 from the home position into the engaged position. Second, tension in cable 486 causes follower pulley 302 and drive pulley 304 and drive pulley 303 to rotate clockwise for approximately 180 degrees, which disengages pawl 312 from drive notch 205 of curved needle 202 and repositions actuator arm 311 to the needle-driving position so that pawl 312 engages drive notch 206 of the curved needle 202. Third, tension in cable 484 causes follower pulley 302, drive pulley 304, and drive pulley 303 to rotate counterclockwise for approximately 180 degrees to again move actuator arm 311 to the needle-ending position and drive curved needle 202 via drive notch 206 from the engaged position back into the home position. Fourth, tension in cable 486 causes follower pulley 302, drive pulley 304, and drive pulley 303 to rotate clockwise for approximately 180 degrees, which disengages pawl 312 from drive notch 206 and repositions actuator arm 311 to the needle-driving position so that pawl 312 again engages drive notch 205.

In the embodiments described above, cables are employed to cause drive mechanism 300 to rotationally actuate curved needle 202. In other embodiments, any other technically feasible actuation apparatus can be employed to cause drive mechanism 300 to rotationally actuate curved needle 202. For example, in one such embodiment, one or both of follower pulley 302 and drive pulley 304 and/or additional drive pulley 303 is motorized. Additionally or alternatively, in one such embodiment, belt drives and/or gears are employed in drive mechanism 300 to rotationally actuate curved needle 202 in addition to or in lieu of cables 484 and 486. A more detailed description of the configuration and operation of an end effector that includes a curved needle and drive mechanism for minimally invasive stitching can be found in U.S. Pat. No. 8,123,764, which is incorporated in its entirety herein.

Figure 6:
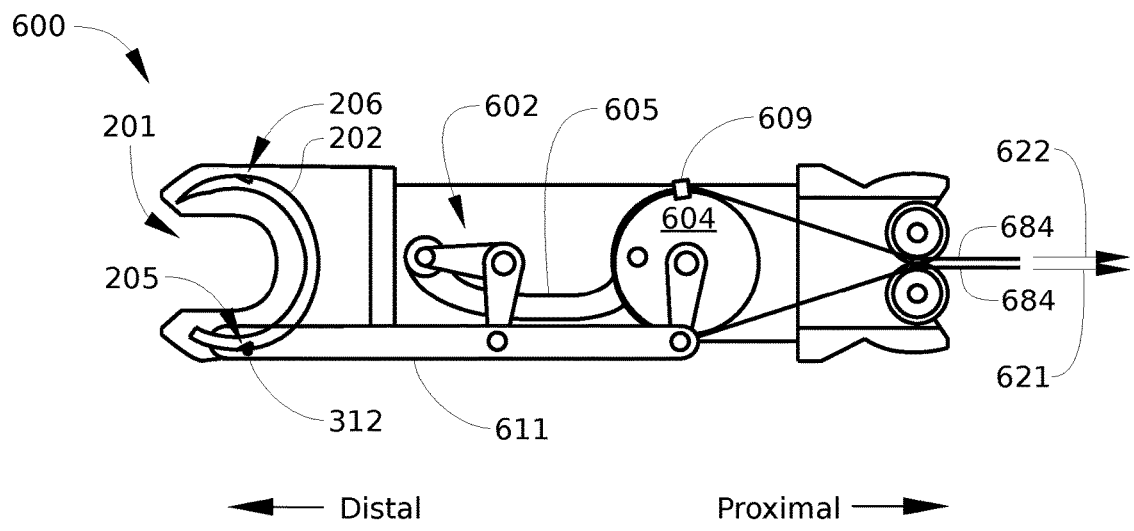
FIG. 6 shows elements of a drive mechanism of an end effector according to some embodiments.

FIG. 6 shows elements of a drive mechanism 600 of end effector 200, configured according to some embodiments. A housing of drive mechanism 600 is omitted in FIG. 6 for clarity. In the embodiment illustrated in FIG. 6, drive mechanism 600 includes a follower pulley 602, a drive pulley 604, and link arm 605 that connects follower pulley 602 and drive pulley 604. In FIG. 6, drive pulley 602 is configured as a pulley element with connector arms in lieu of a disk-shaped body. In other embodiments, drive pulley 602 may be configured with a disk-shaped body. Drive pulley 604 may be connected to a single cable 684, for example via a crimp connector 609. Alternatively, drive pulley 604 may be connected to two cables (e.g., tensed in opposite directions). Alternatively, cable 684 can be implemented as one or more belts. Similar to drive mechanism 300 of FIG. 3, follower pulley 602 and drive pulley 604 are rotationally coupled and therefore rotate in sync together, causing an actuator arm 611 to alternately engage drive notch 205 or 206 on curved needle 202 with pawl 312. Specifically, counterclockwise rotation of follower pulley 602 and drive pulley 604 for 180 degrees drives curved needle 202 through an arc of 180 degrees of rotation drive notch 205 or 206. Conversely, clockwise rotation of follower pulley 602 and drive pulley 604 for 180 degrees disengages pawl 312 from drive notch 205 or 206 and returns actuator arm 611 to the needle-driving position, which is shown in FIG. 6.

In operation of drive mechanism 600, a stitching cycle is completed via drive mechanism 600 in four steps by reciprocally actuating actuator arm 611 around the needle track while keeping actuator arm 611 clear of stitching aperture 201. First, with actuator arm 611 in the needle-driving position and pawl 312 engaged with drive notch 205 of curved needle 202, tension 621 in cable 684 causes follower pulley 602 and drive pulley 604 to rotate counterclockwise for approximately 180 degrees. Actuator arm 611 is thereby moved to the needle-ending position and curved needle 202 is driven from the home position into the engaged position. Second, tension 622 in cable 684 causes follower pulley 602 and drive pulley 604 to rotate clockwise for approximately 180 degrees, which disengages pawl 312 from drive notch 205 of curved needle 202 and repositions actuator arm 611 from the needle-ending position to the needle-driving position, so that pawl 312 engages drive notch 206 of curved needle 202. Third, tension 621 in cable 684 causes follower pulley 602 and drive pulley 604 to rotate counterclockwise for approximately 180 degrees, thereby causing actuator arm 611 to move to the needle-ending position and causing curved needle 202 via drive notch 206 to move from the engaged position back into the home position. Fourth, tension 622 in cable 684 causes follower pulley 602 and drive pulley 604 to rotate clockwise for approximately 180 degrees, which disengages pawl 312 from drive notch 206 and repositions actuator arm 611 back to the needle-driving position, so that pawl 312 again engages drive notch 205.

Optionally, in some embodiments, drive mechanisms 300, 600 may include one or more gears coupling the drive pulleys 303, 304, 604 with the respective follower pulleys 302, 602. Referring by way of example to drive mechanism 600, drive pulley 604 and follower pulley 602 may be coupled to each other by one or more gears instead of link arm 605. For example, drive pulley 604 may be coupled to a first gear having an axis of rotation that coincides with an axis of rotation of drive pulley 604, and follower pulley 602 may be coupled to a second gear having an axis of rotation that coincides with an axis of rotation of the follower pulley 602. The first gear and the second gear may be intermeshed or may be coupled via one or more intermediate gears. In operation, the drive pulley 604 may be driven by cable 684, with rotation of drive pulley 604 causing rotation of the first gear, which thereby causes rotation of the second gear and follower pulley 602 (which may be through one or more intermediate gears).

Figure 7:
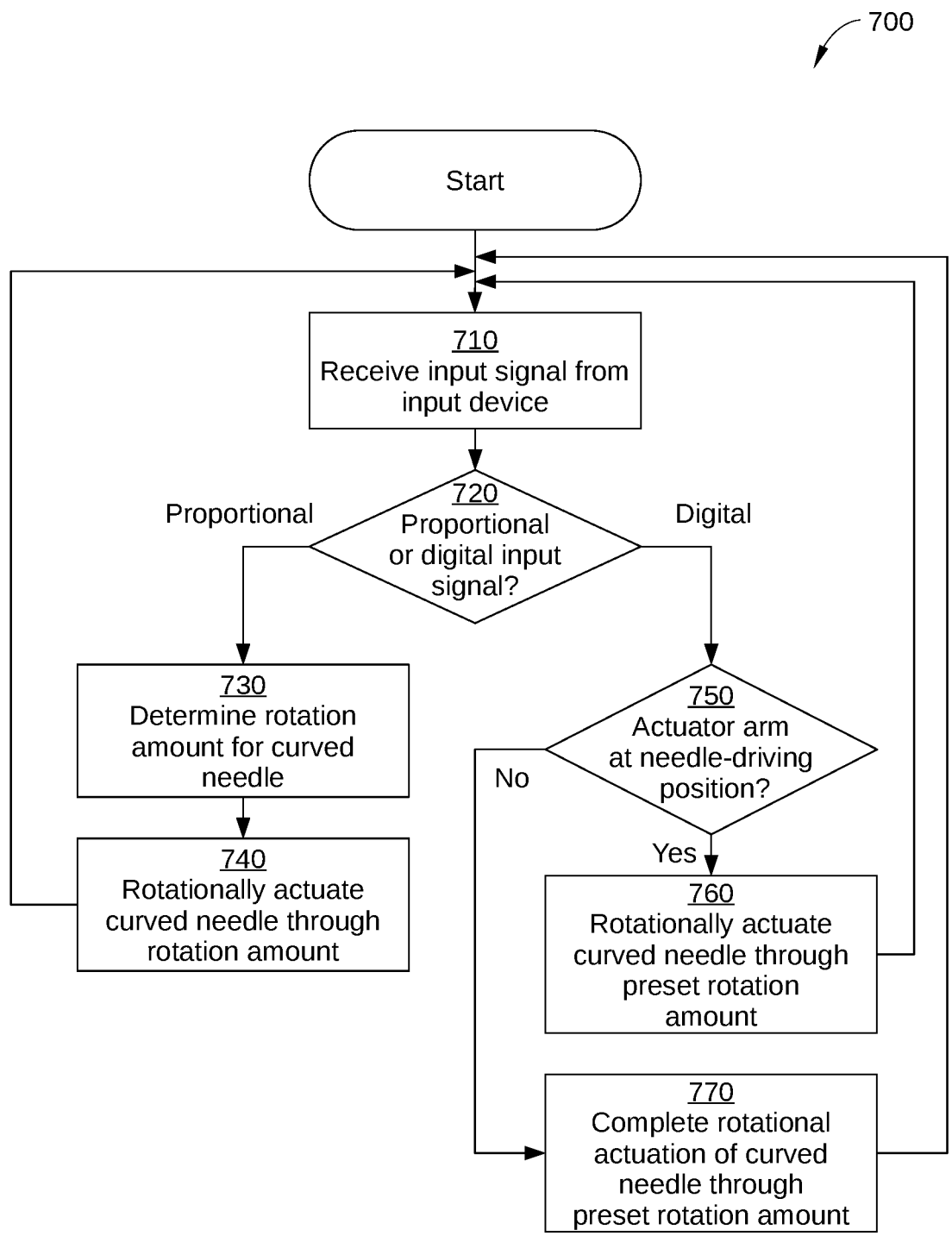
FIG. 7 is a simplified diagram of a method of automated rotation of a needle in a computer-assisted system according to some embodiments.

FIG. 7 is a simplified diagram of a method 700 of automated rotation of a needle in a computer-assisted system, according to some embodiments. One or more of the processes 710-770 of method 700 may be implemented, at least in part, in the form of executable code stored on non-transient, tangible, machine readable media that when run by one or more processors (e.g., the processor 140 in control unit 130) may cause the one or more processors to perform one or more of the processes 710-770. In some embodiments, the method 700 may be performed by control unit 130 and an application, such as motion control application 160.

At a process 710, an input signal (e.g., an input) is received from an input device, such as a continuous motion input device 181 or a digital input device 182.

At a process 720, the determination is made whether the input received at process 710 is a proportional input signal or a digital input signal. In an instance in which the input signal received is generated by a continuous motion input device 181, such as a gripping controller or a rotary controller, the input signal is determined to be a proportional input signal and method 700 proceeds to process 730. In an instance in which the input signal received is generated by a digital input device 182, such as a foot pedal or button, the input signal is determined to be a digital input signal and method 700 proceeds to process 750. In an instance in which both a digital input signal and a continuous input signal are received concurrently, an input priority may indicate which of the two signals to respond to. For example, in some embodiments, a digital input signal is given priority over a concurrent continuous input signal, so that the digital input signal is acted upon and the continuous input signal is not acted upon.

At a process 730, an arc of rotation of curved needle 202 is determined based on mapping 170 and the proportional input signal. For example, in an embodiment in which the continuous motion input device 181 is a gripping controller, the input signal received is proportional in value to how much an operator has closed the gripping controller. Thus, in such an embodiment, when an operator closes the gripping controller 25%, the proportional input signal has a value representing 25% of a maximum available value. In some embodiments, the maximum available value is 180 degrees of rotational actuation of curved needle 202. In such an embodiment, when the proportional input signal has a value corresponding to 25% of the gripping motion being performed by the operator, the arc of rotation determined in process 730 is 45 degrees and when the proportional input signal has a value corresponding to 100% of the gripping motion being performed by the operator, the arc of rotation determined in process 730 is 180 degrees. In other embodiments, the maximum available value is 360 degrees of rotational actuation of curved needle 202. Consequently, in such an embodiment, when the proportional input signal has a value corresponding to 25% of the gripping motion being performed by the operator, the arc of rotation determined in process 730 is 90 degrees and when the proportional input signal has a value corresponding to 100% of the gripping motion being performed by the operator, the arc of rotation determined in process 730 is 360 degrees.

At process 740, drive mechanism 300 is caused to rotationally actuate curved needle 202 through the arc of rotation determined in process 730. Method 700 then proceeds back to process 710.

At process 750, the determination is made whether the current position of actuator arm 311 is at the needle-driving position. If yes, method 700 proceeds to process 760; if no, method 700 proceeds to process 770.

At process 760, drive mechanism 300 is caused to rotationally actuate curved needle 202 through a preset arc of rotation, for example 180 degrees or 360 degrees. In some embodiments, the preset arc of rotation is selected based on which digital input device 182 generates the input signal received in process 710. For example, in an embodiment, operator depression of a first pedal generates a digital input signal associated with causing a rotational actuation of curved needle 202 of 180 degrees, while operator depression of a second pedal generates a digital input signal associated with causing a rotational actuation of curved needle 202 of 360 degrees. Upon completion of process 760, method 700 returns back to the start of method 700.

In one example, to cause rotational actuation of 180 degrees, follower pulley 302, drive pulley 304, and drive pulley 303 of drive mechanism 300 are rotated counterclockwise for approximately 180 degrees, for example via tension in cable 484. The resultant motion of actuator arm 311 (i.e., from the needle-driving position to the needle-ending position) drives curved needle 202 from the home position into the engaged position. Follower pulley 302 and drive pulleys 303 and 304 of drive mechanism 300 are then rotated clockwise for approximately 180 degrees, for example via tension in cable 486. The resultant motion of actuator arm 311 (i.e., from the needle-ending position to the needle-driving position) disengages pawl 312 from drive notch 205 of the curved needle 202, repositions actuator arm 311 to the needle-driving position without repositioning the curved needle 202, and engages pawl 312 with drive notch 206 of the curved needle 202.

In another example, to cause rotational actuation of 360 degrees, follower pulley 302, drive pulley 304, and drive pulley 303 are rotated counterclockwise for approximately 180 degrees and then clockwise for approximately 180 as described above. Then the process is repeated, so that curved needle 202 is driven via drive notch 206 from the engaged position back into the home position, and actuator arm 311 is repositioned back to the needle-driving position.

At process 770, drive mechanism 300 is caused to complete a remainder portion of rotational actuation of curved needle 202 through a preset rotation amount about axis 203, such as for instances where actuator arm 311 is not in the needle-driving position. For example, in one instance, the preset rotation amount about axis 203 is 180 degrees. Further, in response to a proportional input signal being received, certain rotational actuation of drive mechanism 300 occurs (e.g., 45 degrees), and curved needle 202 is driven through a portion of the preset rotation amount about axis 203. In such an instance, when a digital input signal is subsequently received at process 710, process 770 then occurs, in which drive mechanism 300 is caused to complete the remainder portion of rotational actuation of curved needle 202 associated with that digital input signal (i.e., 135 degrees in this example).

Thus, at process 770, when actuator arm 311 is not disposed in the needle-driving position (e.g., due a previously received proportional input signal) and a digital input signal is received that is associated with rotation of curved needle 202 through a preset rotation amount, drive mechanism 300 rotationally actuates curved needle 202 through the remainder portion of the preset rotation amount in response to the digital input signal. In this way, upon completion of process 770, curved needle 202 is driven to either the home position or the engaged position and does not remain in an intermediate position therebetween. Upon completion of process 770, method 700 returns back to the start of method 700.

Figure 8:
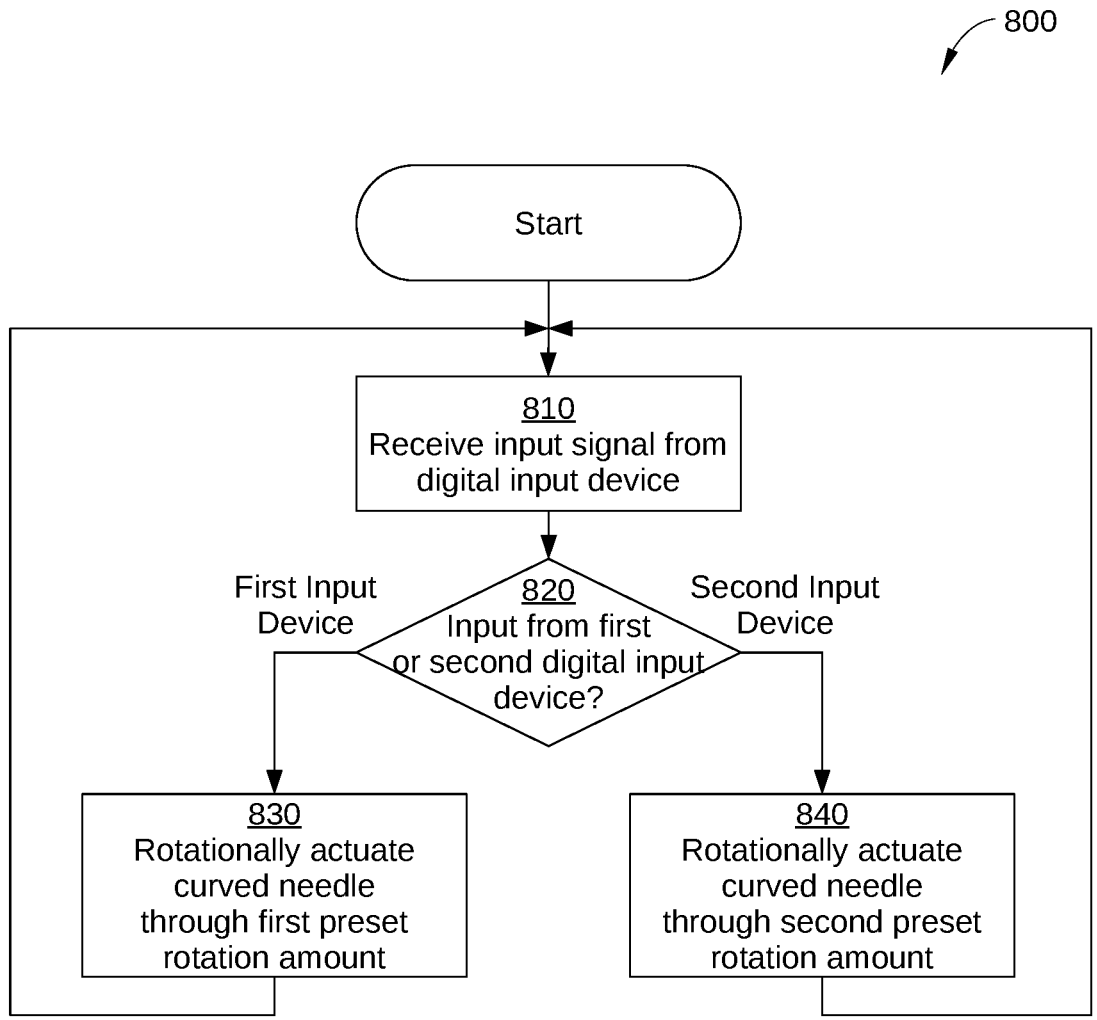
FIG. 8 is a simplified diagram of a method of automated rotation of a needle in a computer-assisted system, according to some embodiments.

FIG. 8 is a simplified diagram of a method 800 of automated rotation of a needle in a computer-assisted surgical system, according to some embodiments. One or more of the processes 810-840 of method 800 may be implemented, at least in part, in the form of executable code stored on non-transient, tangible, machine readable media that when run by one or more processors (e.g., the processor 140 in control unit 130) may cause the one or more processors to perform one or more of the processes 810-840. In some embodiments, the method 800 may be performed by an application, such as motion control application 160.

At a process 810, an input signal is received from an input device, such as a digital input device 182.

At a process 820, the determination is made whether the input received at process 810 is a digital input signal from a first digital input device 182 or a second digital input device 182. In some embodiments, first digital input device 182 is a first foot-operated pedal or floor button and second digital input device 182 is a second foot-operated pedal or floor button. When the input received is from the first digital input device 182, method 800 proceeds to process 830; when the input received is from the second digital input device 182, method 800 proceeds to process 840.

At a process 830, drive mechanism 300 is caused to rotationally actuate curved needle 202 through a first preset arc of rotation, for example 180 degrees. In some embodiments, process 840 is substantially similar to the process of causing rotational actuation of 180 degrees of curved needle 202 described in process 760 of FIG. 7. At process 830, the preset arc of rotation is selected based on which digital input device 182 generates the input signal received in process 810. Upon completion of process 830, method 800 returns back to the start of method 800.

At a process 840, drive mechanism 300 is caused to rotationally actuate curved needle 202 through a second preset arc of rotation, for example 360 degrees. In some embodiments, process 840 is substantially similar to the process of causing rotational actuation of 360 degrees of curved needle 202 described in process 760 of FIG. 7. At process 840, the preset arc of rotation is selected based on which digital input device 182 generates the input signal received in process 810. Upon completion of process 840, method 800 returns back to the start of method 800.

Figure 9:
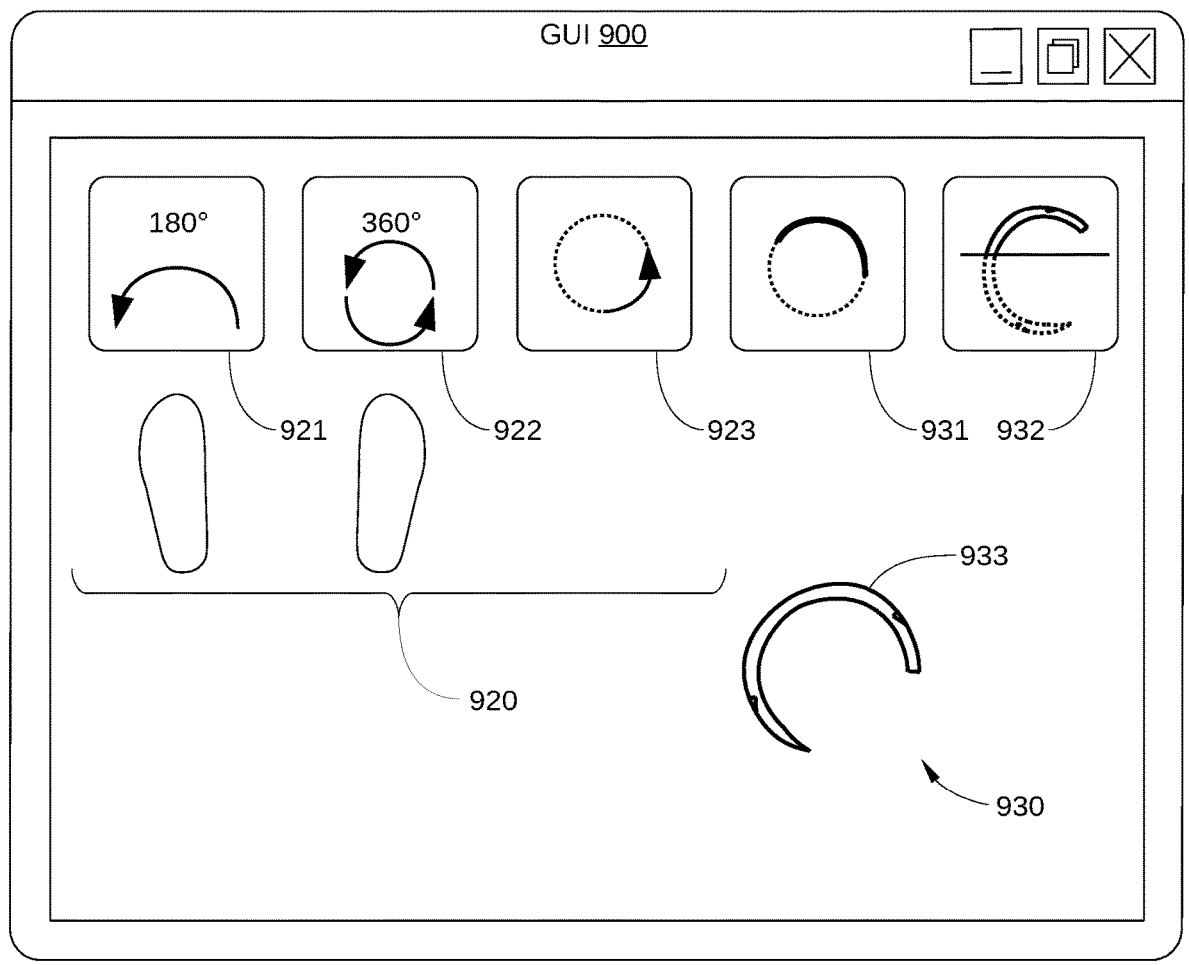
FIG. 9 is a schematic illustration of a graphical user interface for interaction with a computer-assisted device, according to various embodiments.

In some embodiments, GUI 190 includes one or more visual elements that facilitate operator interaction with a computer-assisted device. One such embodiment is described below in conjunction with FIG. 9. FIG. 9 is a schematic illustration of a GUI 900 for interaction with a computer-assisted device, according to various embodiments. In some embodiments, the computer assisted device may correspond to computer-assisted device 110 of FIG. 1. In some embodiments, some or all features of GUI 900 are implemented as a separate screen or window from other screens employed by an operator during use of the computer-assisted device. Alternatively or additionally, in some embodiments some or all features of GUI 900 are implemented as visual elements that are incorporated into or superimposed on information normally displayed to an operator. In FIG. 9, GUI 900 is depicted as a separate window.

As shown, GUI 900 includes one or more icons 920 that indicate what needle actuation controls are available to the operator. For example, in some embodiments, a half-rotation icon 921 indicates whether a digital input device 182 is available for causing a 180-degree rotation of curved needle 202 to occur; a full-rotation icon 922 indicates whether a digital input device 182 is available for causing a 360-degree rotation of curved needle 202 to occur; and/or a proportional motion icon 923 indicates whether a proportional input signal from a continuous motion input device 181 can be employed by the operator.

In some embodiments, GUI 900 includes one or more icons 930 that indicate current status information associated with stitching operations being performed by the operator, such as a rotational indicator icon 931, a needle engagement icon 932, and/or a needle location image 933. In some embodiments, rotational indicator icon 931 or other indicator displays information indicating the current rotational progress or arc of rotation completed. In such embodiments, the information displayed may be based on the current rotational displacement of a drive mechanism, such as one of follower pulley 302 or drive pulley 304 of FIG. 3. In some embodiments, needle engagement icon 932 or other indicator displays information indicating curved needle 202 is currently at least partially engaged with a material, such as tissue in a medical example. In such embodiments, the information displayed may be based on electrical and/or mechanical feedback that occurs when curved needle 202 has engaged with the material. In some embodiments, a needle location image 933 or other indicator is superimposed in images of the current worksite, for example to indicate a current location of curved needle 202 when engaged in material and is not visible to the operator. In such embodiments, the needle location information displayed may be based on the current rotational displacement of a drive mechanism, such as one of follower pulley 302 or drive pulley 304 of FIG. 3.

In some embodiments, a drive mechanism of an end effector in a device, such as device 110 of FIG. 1, is configured to provide retraction (e.g., backward) rotary motion of a curved needle in addition to forward rotary motion of the curved needle. Thus, in such embodiments, mechanical coupling between the rotary actuation elements of the drive mechanism and the curved needle can both push and pull the curved needle, for example via a pawl or other feature coupled to the curved needle. Further, in such embodiments, a continuous motion input device (e.g., continuous motion input device 181 of FIG. 1) is configured to be continuously movable in two opposing directions and to generate a corresponding proportional input signal. By way of a non-limiting example, the curved needle may have a home position in which the curved needle is completely within the housing of the drive mechanism and an engaged position in which the curved needle extends from the housing and across aperture 201 (as shown in FIG. 2) to engage in tissue. In some embodiments, the engaged position may correspond to the curved needle rotating approximately 180 degrees relative to the home position. The embodiments described herein enable an operator to "peek" the curved needle out of the home position and into a tissue gap area of the end effector (such as stitching aperture 201 shown in FIG. 2) via actuation of the continuous motion input device in one direction. A peek of the needle may correspond to a needle leading edge position that is between the home position and the engaged position. As a result, operator visualization of the curved needle before instituting a loop with a digital input is enabled. In such embodiments, the operator can then retract the curved needle back to the home position via actuation of the continuous motion input device in an opposite direction prior to causing autonomous rotation of the curved needle via a digital input.

In embodiments in which continuous motion device 181 is implemented as a rotary input device, continuous motion device 181 is configured to be continuously movable in both the clockwise and the counterclockwise directions. In such embodiments, a proportional input signal from the continuous motion device 181 being actuated in the clockwise direction indicates one of forward rotary motion or retraction rotary motion of the curved needle, and a proportional input signal from the continuous motion device 181 being actuated in the clockwise direction indicates the opposing rotary motion of the curved needle. In some embodiments, retraction rotary motion of the curved needle beyond a home position can be indicated by rotation of the rotary input device beyond a corresponding "0" position. In such embodiments, the proportional input signal from the continuous motion device 181 may indicate a negative value (e.g., −25%) that causes the curved needle to retract further backwards beyond the home position. In such embodiments, mapping 170 of the proportional input signal from the rotary input device to rotational arc amounts of the curved needle may include such negative values.

In embodiments in which continuous motion device 181 is implemented as a gripping controller, continuous motion device 181 is configured to be continuously movable from a 0% open gripping position to a 100% closed gripping position. In such embodiments, a proportional input signal from the continuous motion device 181 being actuated in the gripping direction indicates forward rotary motion of the curved needle, and a proportional input signal from the continuous motion device 181 being actuated in the opening direction indicates retraction rotary motion of the curved needle. Thus, in such embodiments, the gripping controller may be mapped between fully open (0% of travel) and fully closed (100% of travel). An operator can partially close or actuate the gripping controller (e.g., 25% closed) from a home position to cause the curved needle to rotate to a corresponding partially rotated position (e.g., rotated 25% of a 180-degree rotation or a 360-degree rotation), for example, to "peek" the needle outward a desired amount from the housing but less than the engaged position. The operator may then return the curved needle back to the home position by opening the gripping controller back to 0% closed. In such embodiments, mapping 170 of the proportional input signal from the gripping controller to rotational arc amounts of the curved needle can be implemented independently from the direction of rotary motion of the curved needle.

In embodiments in which a drive mechanism of an end effector is configured to provide forward and retraction rotary motion of a curved needle, automated rotation of a needle can be conducted after an operator has caused the curved needle to peek into a tissue gap area of the end effector, for example to perform a 180-degree rotation or a 360-degree rotation of the curved needle.

In some embodiments where a peek is performed, before the automated rotation of the curved needle is performed, the curved needle may either be returned by the operator to the home position or continued to the engaged position via the continuous motion device 181. Optionally, in some embodiments, automated rotation may be disabled while the needle is peeked into the tissue gap area. For example, an operator may actuate a continuous motion device 181 to a needle peek position (e.g., by actuating a gripping controller to 10% of the gripping controller travel). While in the needle peek position, optionally, automated rotation of the curved needle may be disabled. However, upon return of the needle to the home position of the continuous motion device 181 (e.g., 0% of gripping controller travel, or fully open), automated rotation may be re-enabled. The user may alternatively re-enable automated rotation by instead using the continuous motion device 181 to move the needle to the engaged position (100% of gripping controller travel, or fully closed). In such embodiments, the automated rotation of the curved needle is not conducted unless the gripping controller (or other continuous motion device 181) is returned to a position at or near the non-actuation position, or moved to a position at or near the engaged position. One such embodiment is described below in conjunction with FIG. 10.

Figure 10:
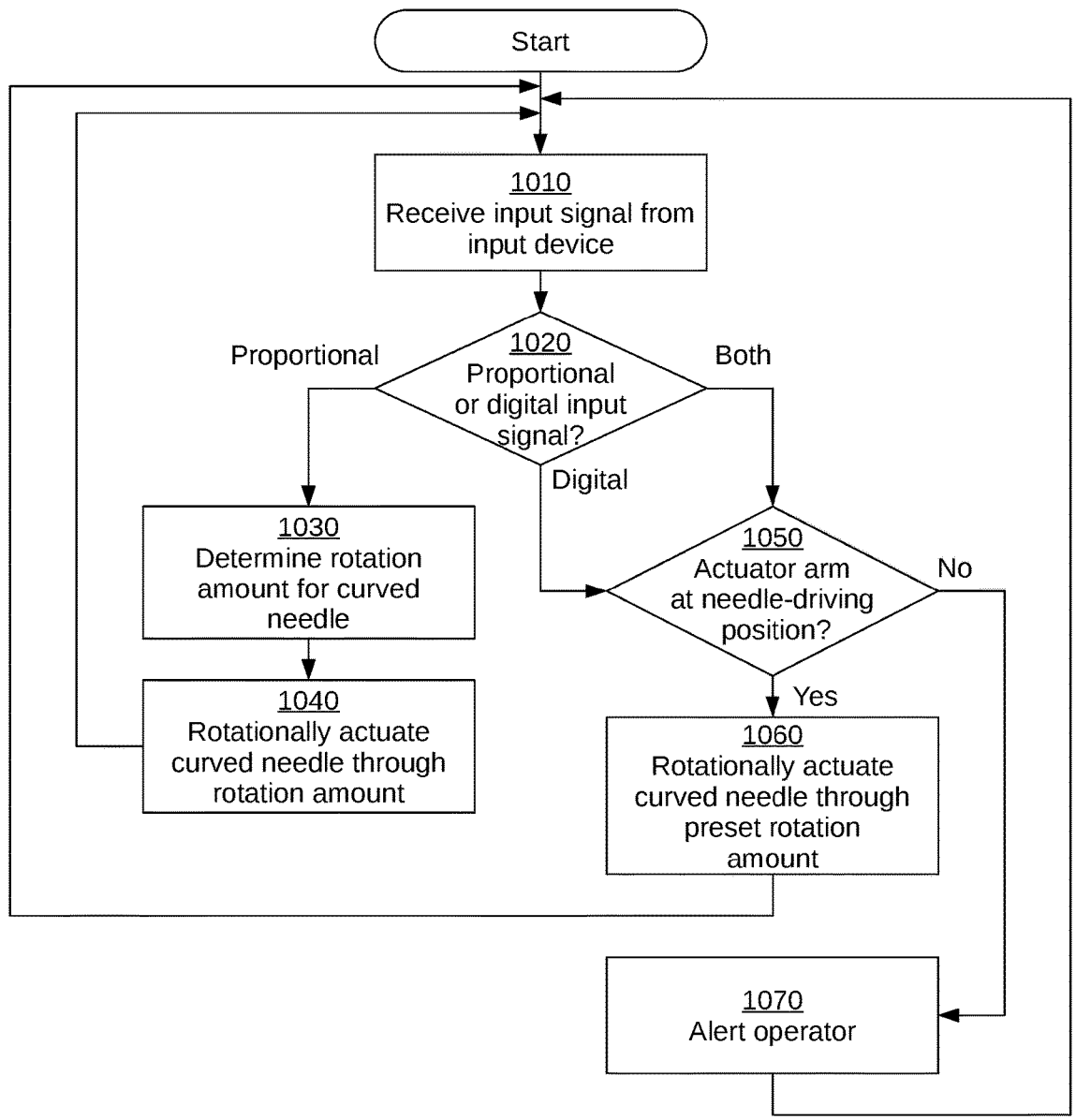
FIG. 10 is a simplified diagram of a method of automated rotation of a needle in a computer-assisted system, according to some embodiments.

FIG. 10 is a simplified diagram of a method of automated rotation of a needle in a computer-assisted system, according to some embodiments. One or more of the processes 1010-1070 of method 1000 may be implemented, at least in part, in the form of executable code stored on non-transient, tangible, machine readable media that when run by one or more processors (e.g., the processor 140 in control unit 130) may cause the one or more processors to perform one or more of the processes 1010-1070. In some embodiments, the method 1000 may be performed by control unit 130 and an application, such as motion control application 160.

At a process 1010, an input signal (e.g., an input) is received from an input device, such as a continuous motion input device 181, a digital input device 182, or a combination of both. It is noted that when a combination of both a digital input signal and a proportional input signal is received at process 1010, generally, the digital input signal is received as an additional input signal while the proportional input signal is already being received. For example, when an operator actuates a continuous motion input device 181 to a certain position (e.g., closing a gripping controller 25%), then actuates a digital input device 182 while actuating the continuous motion device (and thus maintaining the proportional input signal), a combination of both a digital input signal and a proportional input signal is received at process 1110.

At a process 1020, the determination is made whether the input received at process 1010 is a proportional input signal, a digital input signal, or a combination of both. In an instance in which the input signal received is generated by a continuous motion input device 181, such as a gripping controller or a rotary controller, the input signal is determined to be a proportional input signal and method 1000 proceeds to process 1030. In an instance in which the input signal received is generated by a digital input device 182, such as a foot pedal or button, the input signal is determined to be a digital input signal and method 1000 proceeds to process 1050. In an instance in which both a digital input signal and a continuous input signal are received concurrently, method 1000 proceeds to process 1050.

At a process 1030, an arc of rotation of curved needle 202 is determined based on mapping 170 and the proportional input signal. In some embodiments, process 1030 is substantially similar to process 730 in method 700 of FIG. 7.

At process 1040, drive mechanism 300 is caused to rotationally actuate curved needle 202 through the arc of rotation determined in process 1030. In some embodiments, process 1040 is substantially similar to process 740 in method 700 of FIG. 7. Method 1000 then returns to process 1010.

At process 1050, the determination is made whether the current position of actuator arm 311 is at (or within a predetermined tolerance from) a needle-driving position. If yes, method 1000 proceeds to process 1060; if no, method 1000 proceeds to process 1070.

At process 1060, drive mechanism 300 is caused to rotationally actuate curved needle 202 through a preset arc of rotation, for example 180 degrees or 360 degrees. In some embodiments, process 1060 is substantially similar to process 760 in method 700 of FIG. 7. Upon completion of process 1060, method 1000 returns back to the start of method 1000.

At process 1070, the operator is alerted. For example, in some embodiments, the alert can be provided to the operator via one or more of a visual display (via icons and/or text), a playing of an audio message, and/or a haptic feedback. In some embodiments, the alert indicates that rotational actuation of curved needle 202 through a preset arc of rotation cannot occur until the current position of actuator arm 311 is at (or within a predetermined tolerance from) a needle-driving position (e.g., the home position). Alternatively or additionally, in some embodiments, the alert prompts the operator to actuate continuous motion input device 181 to a 0% position of the input range of the continuous motion input device 181. In some embodiments, the alert may alternatively or additionally inform the user that actuation of continuous motion input device 181 to a 100% position of its input range is permitted (e.g., corresponding to the engaged position). Method 1000 then returns back to process 1010.

As noted above, in some embodiments, a drive mechanism of an end effector is configured to provide forward and retraction rotary motion of a curved needle, and automated rotation of a needle can be conducted after an operator has caused the curved needle to peek into a tissue gap area of the end effector, for example to perform a 180-degree rotation or a 360-degree rotation of the curved needle. In some embodiments, the automated rotation of the curved needle is initiated while the curved needle is still disposed in the tissue gap of the end effector. Thus, in such embodiments, the automated rotation of the curved needle is performed even though the gripping controller (or other continuous motion device 181) has not been returned to a position at or near the non-actuation position or to the engaged position. One such embodiment is described below in conjunction with FIG. 11.

Figure 11:
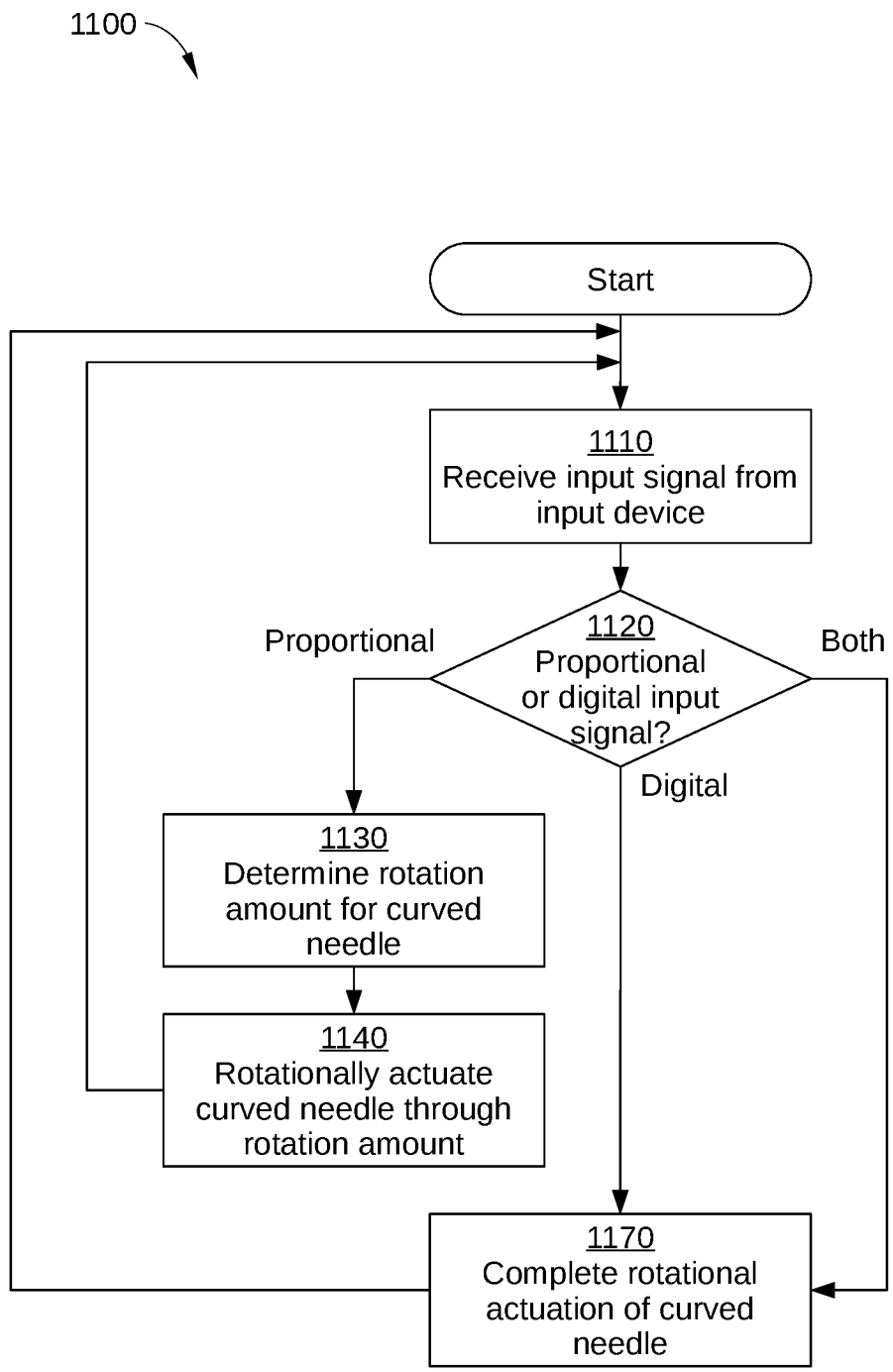
FIG. 11 is a simplified diagram of a method of automated rotation of a needle in a computer-assisted system, according to some embodiments.

FIG. 11 is a simplified diagram of a method of automated rotation of a needle in a computer-assisted system, according to some embodiments. One or more of the processes 1110-1170 of method 1100 may be implemented, at least in part, in the form of executable code stored on non-transient, tangible, machine readable media that when run by one or more processors (e.g., the processor 140 in control unit 130) may cause the one or more processors to perform one or more of the processes 1110-1170. In some embodiments, the method 1100 may be performed by control unit 130 and an application, such as motion control application 160.

At a process 1110, an input signal (e.g., an input) is received from an input device, such as a continuous motion input device 181, a digital input device 182, or a combination of both. It is noted that when a combination of both a digital input signal and a proportional input signal is received at process 1110, generally, the digital input signal is received as an additional input signal while the proportional input signal is already being received. For example, when an operator actuates a continuous motion input device 181 to a certain position (e.g., closing a gripping controller 25%), then actuates a digital input device 182 while actuating the continuous motion device (and thus maintaining the proportional input signal), a combination of both a digital input signal and a proportional input signal is received at process 1110.

At a process 1120, the determination is made whether the input received at process 1110 is a proportional input signal, a digital input signal, or a combination of both. In an instance in which the input signal received is generated by a continuous motion input device 181, such as a gripping controller or a rotary controller, the input signal is determined to be a proportional input signal and method 1100 proceeds to process 1130. In an instance in which the input signal received is generated by a digital input device 182, such as a foot pedal or button, the input signal is determined to be a digital input signal and method 1100 proceeds to process 1170. In an instance in which both a digital input signal and a continuous input signal are received concurrently, method 1100 proceeds to process 1170.

At a process 1130, an arc of rotation of curved needle 202 is determined based on mapping 170 and the proportional input signal. In some embodiments, process 1130 is substantially similar to process 730 in method 700 of FIG. 7.

At process 1140, drive mechanism 300 is caused to rotationally actuate curved needle 202 through the arc of rotation determined in process 1130. In some embodiments, process 1140 is substantially similar to process 740 in method 700 of FIG. 7. Method 1100 then returns to process 1110.

At process 1170, drive mechanism 300 is caused to complete rotational actuation of curved needle 202 through a preset arc of rotation, for example 180 degrees or 360 degrees. In some embodiments, process 1170 is substantially similar to processes 760 and/or 770 in method 700 of FIG. 7. In some embodiments, at process 1170, drive mechanism 300 is caused to complete a remainder portion of rotational actuation of curved needle 202. In such embodiments, completion of the rotational actuation of curved needle 202 entails rotational actuation through a remainder portion of a preset rotation amount about axis 203, such as for instances where actuator arm 311 is not in the home position. Thus, in such embodiments, the digital input received in process 1110 results in rotation of less than a preset rotation amount about axis 203, such as the preset rotation amount about axis 203 minus the amount of rotational actuation performed of the curved need after completing process 1140. Method 1100 then returns to process 1110.

In some embodiments, use of autonomous rotational actuation of curved needle 202 in conjunction with an operator peeking curved needle 202 out of a home position (via actuation of continuous motion input device 181) is facilitated by a remapping of values of a proportional input signal from continuous motion input device 181. In such embodiments, an operator can peek curved needle 202 into a tissue gap area of the end effector via continuous motion input device 181, then cause a digital input signal to be generated via digital input device 182 while continuing to hold the same position for continuous motion input device 181. In such embodiments, the digital input motion causes autonomous rotational actuation of curved needle 202, so that curved needle 202 is rotated about axis 203 until a preset rotation amount is completed, such as a 180-degree or 360-degree rotation amount. In such embodiments, a remapping of the proportional input signal from continuous motion input device 181 is performed, in which the remaining continuous motion travel available for continuous motion input device 181 is mapped to 0% to 100% of the travel of curved needle 202. Thus, in such embodiments, after the autonomous rotational actuation of curved needle 202 occurs and curved needle 202 is rotated until the preset rotation amount is completed, an operator can peek curved needle 202 into the tissue gap area of the end effector via continuous motion input device 181 again, without first resetting continuous motion input device 181 back to a 0% closed (e.g., home) position. For example, in an embodiment in which continuous motion input device 181 is implemented as a gripping controller, an operator can close the gripping controller to a 10% closed position to peek curved needle 202 into the tissue gap and cause autonomous rotational actuation of curved needle 202 with digital input device 182 while continuing to hold the gripping controller at the 10% closed position. In response to the gripping controller being maintained at the 10% closed position while a digital input signal is received from digital input device 182, a modified mapping of values included in mapping 170 is generated. In some embodiments, mapping 170 is modified to include a modified mapping of values of the proportional input signal from continuous motion input device 181 to values of a rotational arc amount of curved needle 202 that is based on the proportional input signal received while the digital input signal is received from digital input device 182. Thus, in an example, in mapping 170, values of the proportional input signal corresponding to 10% to 100% of gripping controller closure are mapped to values corresponding to 0% to 100% of the preset rotation amount of curved needle 202. Therefore, in such an example, 10% closure of the gripping controller is mapped to curved needle 202 being positioned at a 0% (home) position. Based on the modified mapping, the operator can then close the gripping controller from the 10% closed position to a 20% closed position to again peek curved needle 202 into the tissue gap (e.g., to 11% of the preset rotation amount) and again cause autonomous rotational actuation of curved needle 202 with digital input device 182 while continuing to hold the gripping controller at the 20% closed position. In response to the gripping controller being maintained at the 20% closed position while a digital input signal is received from digital input device 182, another modified mapping of values included in mapping 170 is generated. Such a process can continue until an operator resets the mapping of the proportional input signal from continuous motion input device 181 by opening the gripping controller to the 0% closed position, at which point values included in mapping 170 are reset to an original mapping. One such embodiment is described below in conjunction with FIG. 12.

Figure 12:
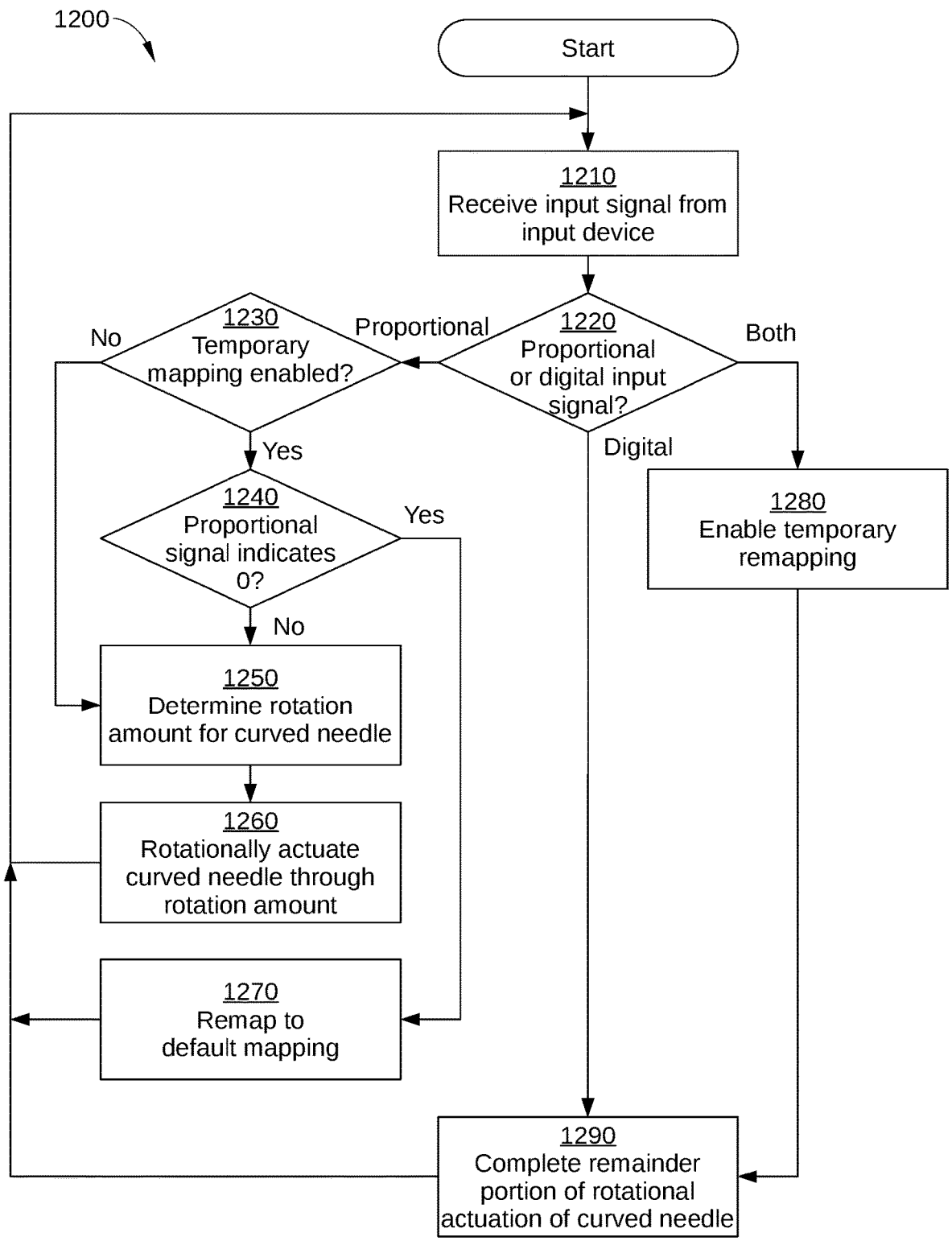
FIG. 12 is a simplified diagram of a method of automated rotation of a needle in a computer-assisted system, according to some embodiments.

FIG. 12 is a simplified diagram of a method of automated rotation of a needle in a computer-assisted system, according to some embodiments. One or more of the processes 1210-1290 of method 1200 may be implemented, at least in part, in the form of executable code stored on non-transient, tangible, machine readable media that when run by one or more processors (e.g., the processor 140 in control unit 130) may cause the one or more processors to perform one or more of the processes 1210-1290. In some embodiments, the method 1200 may be performed by control unit 130 and an application, such as motion control application 160.

At a process 1210, an input signal (e.g., an input) is received from an input device, such as a continuous motion input device 181, a digital input device 182, or a combination of both. In some embodiments, process 1210 is substantially similar to process 1110 in method 1100 of FIG. 11.

At a process 1220, the determination is made whether the input received at process 1210 is a proportional input signal, a digital input signal, or a combination of both. In an instance in which the input signal received is generated by a continuous motion input device 181, such as a gripping controller or a rotary controller, the input signal is determined to be a proportional input signal and method 1200 proceeds to process 1230. In an instance in which the input signal received is generated by a digital input device 182, such as a foot pedal or button, the input signal is determined to be a digital input signal and method 1200 proceeds to process 1250. In an instance in which both a digital input signal and a continuous input signal are received concurrently, method 1200 proceeds to process 1280.

At a process 1230, the determination is made whether a temporary remapping of mapping 170 has been enabled. If yes, method 1200 proceeds to process 1240; if no, method 1200 proceeds to process 1250.

At a process 1240, the determination is made whether the proportional input signal received in process 1210 indicates a return to a zero or home position. If yes, method 1200 proceeds to process 1270; if no, method 1200 proceeds to process 1250.

At a process 1270, mapping 170 is returned to an original mapping of values of a proportional input signal received from continuous motion input device 181 to a particular rotational arc amount. In some embodiments, the original mapping maps values of the full input range of proportional input signal (e.g., 0% to 100%) to values of a preset rotational arc amount of the curved needle, e.g., a 180-degree or 360-degree rotation amount. Thus, in such embodiments, a value corresponding to a 0% proportional input signal (e.g., a gripping controller 0% closed) is mapped to 0% of the preset rotational arc amount (e.g. 0 degrees rotation of curved needle 202), and a value corresponding to a 100% proportional input signal (e.g., a gripping controller 100% closed) is mapped to 100% of the preset rotational arc amount (e.g. 180 degrees or 350 degrees of rotation of curved needle 202). Method 1200 then returns back to process 1210.

At a process 1250, an arc of rotation of curved needle 202 is determined based on mapping 170 and the proportional input signal. In some embodiments, process 1250 is substantially similar to process 1130 in method 1100 of FIG. 11, except that a modified mapping 170 may be employed instead of the original mapping 170.

At process 1260, drive mechanism 300 is caused to rotationally actuate curved needle 202 through the arc of rotation determined in process 1250. In some embodiments, process 1260 is substantially similar to process 1140 in method 1100 of FIG. 11. Method 1200 then returns to process 1210.

At process 1280, in response to the proportional input signal being received in combination with the digital input signal, mapping 170 is temporarily modified. Specifically, the values of the proportional input signal from continuous motion input device 181 are remapped to different rotational arc amounts. In some embodiments, the value of the proportional input signal received in combination with the digital input signal is remapped to 0 rotational arc and the maximum available value of the proportional input signal (e.g., 100% gripping motion) received in combination with the digital input signal is mapped to a preset rotation amount about axis 203, such as a 180-degree or 360-degree rotation amount. Method 1200 then returns to process 1210.

At process 1290, drive mechanism 300 is caused to rotationally actuate curved needle 202 through a preset arc of rotation, for example 180 degrees or 360 degrees. In some embodiments, process 1290 is substantially similar to process 1170 in method 1100 of FIG. 11. In some embodiments, at process 1290, drive mechanism 300 is caused to complete a remainder portion of rotational actuation of curved needle 202. In such embodiments, completion of the rotational actuation of curved needle 202 entails rotational actuation through a remainder portion of a preset rotation amount about axis 203, such as for instances where actuator arm 311 is not in the home position when the digital signal is received. Method 1200 then returns to process 1210.

Some examples of control units, such as control unit 130 may include non-transient, tangible, machine readable media that include executable code that when run by one or more processors (e.g., processor 140) may cause the one or more processors to perform the processes of methods 700 and/or 800. Some common forms of machine readable media that may include the processes of methods 700 and/or 800 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

1. In some embodiments, a method in a computer-assisted device that includes an end effector includes: in response to receiving a first input, causing a drive mechanism of the end effector to rotationally actuate a curved needle coupled to the drive mechanism by a first preset rotation amount along an arcuate path; and in response to receiving a second input, causing the drive mechanism to rotationally actuate the curved needle by a second preset rotation amount along the arcuate path.

2. The method of clause 1, wherein the arcuate path comprises a circular path and the drive mechanism is configured to rotationally actuate the curved needle about an axis that includes a center point of the circular path.

3. The method of clause 2, wherein the first preset rotation amount is a 180 degree rotation of the curved needle about the axis.

4. The method of clause 2, wherein the second preset rotation amount is a 360 degree rotation of the curved needle about the axis.

5. The method of clause 1, wherein the first input is received from a first input device and the second input is received from a second input device different from the first input device.

6. The method of clause 1, wherein the first input and the second input are each received from a same input device.

7. The method of clause 5, wherein the first input device comprises a first foot pedal and the second input device comprises a second foot pedal.

8. The method of clause 5, wherein the first input device comprises a first digital button and the second input device comprises a second digital button.

9. The method of clause 1, wherein the computer-assisted device is a surgical device and the curved needle is a curved suturing needle.

10. The method of clause 1, wherein the end effector is configured to be mounted near a distal end of a repositionable arm.

11. The method of any of clauses 1 to 10, wherein the control unit is further configured to, in response to receiving a digital input signal from a second input device, cause the drive mechanism to complete a rotational actuation of the curved needle through a preset rotation amount about an axis.

12. The method of clause 11, wherein the operator input signal and the digital input signal are received concurrently.

13. The method of clause 11, further comprising, to cause the drive mechanism to complete the rotational actuation of the curved needle through the preset rotation amount, causing the drive mechanism to actuate the curved needle through a first rotation amount that is less than the preset rotation amount or more than the preset rotation amount.

14. The method of clause 13, wherein the first rotation amount is based on a rotation amount that corresponds to the operator input signal that is received concurrently with the digital input signal.

15. The method of clause 13, wherein the first rotation amount is based on a difference between the preset rotation amount and a rotation amount that corresponds to the operator input signal that is received concurrently with the digital input signal.

16. The method of clause 13, further comprising, generating a modified mapping of the operator input signal, wherein the modified mapping maps values of the operator input signal to values of a rotational arc amount of the curved needle that is smaller than the preset rotation amount.

17. The method of clause 16, wherein the values of the rotational arc amount of the curved needle that is smaller than the preset rotation amount is based on the operator input signal received concurrently with the digital input signal.

18. The method of clause 16, further comprising, in response to receiving an operator input signal corresponding to a fully open position of a grip controller of the computer-assisted device after the generation of the modified mapping, resetting the mapping of the operator input signal to an original mapping of the values of the operator input signal to the values of the rotational arc amount of the curved needle.

19. The method of clause 16, further comprising, in response to receiving a second operator input signal after receiving the digital input signal: based on the modified mapping, determining an arc of rotation for the curved needle along an arcuate path corresponding to the second operator input signal; and causing the drive mechanism to rotationally actuate the curved needle through the arc of rotation along the arcuate path corresponding to the second operator input signal.

20. The computer-assisted device of any one of clauses 1 to 10, further comprising, in response to receiving a digital input signal from a second input device: determining that the drive mechanism is not disposed within a certain distance of a home position; and preventing the drive mechanism from completing the rotational actuation of the curved needle through a preset rotation amount about the axis.

21. In some embodiments, a method in a computer-assisted device that includes an end effector having a drive mechanism configured to be coupled to a curved needle and configured to rotationally actuate the curved needle along an arcuate path includes: receiving an operator input signal; based on a mapping of the operator input signal to a rotational arc amount of the curved needle, determining an arc of rotation for the curved needle along the arcuate path corresponding to the operator input signal; and causing the drive mechanism to rotationally actuate the curved needle through the arc of rotation along the arcuate path.

22. The method of clause 21, wherein the operator input signal is received from a continuous motion input device.

23. The method of clause 22, wherein the continuous motion input device comprises a rotary input device of a computer-assisted system.

24. The method of clause 23, wherein the mapping maps one revolution of the rotary input device to 360 degrees of rotation for the curved needle.

25. The method of clause 22, wherein the operator input signal is received from a gripping controller of a computer-assisted system.

26. The method of clause 25, wherein the mapping maps movement of the gripping controller from open to closed to 180 degrees or 360 degrees of rotation for the curved needle.

27. The method of clause 21, wherein the arcuate path comprises a circular path and the drive mechanism is configured to rotationally actuate the curved needle about an axis that includes a center point of the circular path.

28. The method of clause 27, wherein the axis is located at a center of a circle defined by a curve of the curved needle.

29. The method of clause 21, wherein the computer-assisted device is a surgical device and the curved needle is a curved suturing needle.

30. The method of clause 21, wherein the end effector is configured to be mounted near a distal end of a repositionable arm.

31. The method of clause 21, wherein the mapping includes a first mapping of a first proportional input signal that is generated by actuation of a continuous motion input device in a first direction and a second mapping of a second proportional input signal that is generated by actuation of the continuous motion input device in a second direction.

32. The method of clause 31, wherein the first mapping maps values of the first proportional input signal to values of a first rotational arc of the drive mechanism and the second mapping maps values of the second proportional input signal to values of a second rotational arc of the drive mechanism.

33. The method of clause 11, further comprising, in response to receiving a digital input signal from a second input device, causing the drive mechanism to complete a rotational actuation of the curved needle through a preset rotation amount about an axis.

34. The method of clause 33, wherein the second input device comprises a digital input device.

35. The method of clause 33, wherein the second input device comprises a foot pedal.

36. The method of clause 33, wherein the preset rotation amount is a 180 degree or a 360 degree rotation of the curved needle about an axis.

37. A non-transitory machine-readable medium comprising a plurality of machine-readable instructions which when executed by one or more processors are adapted to cause the one or more processors to perform the method of any one of clauses 1 to 36.

Although illustrative embodiments have been shown and described, it is to be understood that such embodiments are merely illustrative of and not restrictive on the broad inventive concept. A wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims and equivalents thereof.

What is claimed is:

1. A computer-assisted device comprising:
   an end effector having a drive mechanism configured to be coupled to a curved needle and configured to rotationally actuate the curved needle along an arcuate path; and
   a control unit coupled to the drive mechanism;
   wherein the control unit is configured to:
      in response to receiving a first input, cause the drive mechanism to rotationally actuate the curved needle by a first preset rotation amount along the arcuate path; and
      in response to receiving a second input, cause the drive mechanism to rotationally actuate the curved needle by a second preset rotation amount along the arcuate path,
      wherein the second preset rotation amount differs from the first preset rotation amount.

2. The computer-assisted device of claim 1, wherein the arcuate path comprises a circular path and the drive mechanism is configured to rotationally actuate the curved needle about an axis that includes a center point of the circular path.

3. The computer-assisted device of claim 2, wherein the first preset rotation amount is a 180 degree rotation of the curved needle about the axis along a first direction.

4. The computer-assisted device of claim 3, wherein the second preset rotation amount is a 360 degree rotation of the curved needle about the axis along the first direction.

5. The computer-assisted device of claim 1, wherein the first input is received from a first input device and the second input is received from a second input device different from the first input device.

6. The computer-assisted device of claim 1, wherein the first input and the second input are each received from a same input device.

7. The computer-assisted device of claim 5, wherein the first input device comprises a first foot pedal and the second input device comprises a second foot pedal.

8. The computer-assisted device of claim 5, wherein the first input device comprises a first digital button and the second input device comprises a second digital button.

9. The computer-assisted device of claim 1, wherein the computer-assisted device is a surgical device and the curved needle is a curved suturing needle.

10. The computer-assisted device of claim 1, wherein the end effector is configured to be mounted near a distal end of a repositionable arm.

11. A method comprising:
in response to receiving a first input, causing, by a control unit, a drive mechanism of an end effector of a computer-assisted device to rotationally actuate a curved needle coupled to the drive mechanism by a first preset rotation amount along an arcuate path; and
in response to receiving a second input, causing, by the control unit, the drive mechanism to rotationally actuate the curved needle by a second preset rotation amount along the arcuate path,
wherein the second preset rotation amount differs from the first preset rotation amount.

12. The method of claim 11, wherein the arcuate path comprises a circular path and the drive mechanism is configured to rotationally actuate the curved needle about an axis that includes a center point of the circular path.

13. The method of claim 12, wherein:
the first preset rotation amount is a 180 degree rotation of the curved needle about the axis along a first direction; and
the second preset rotation amount is a 360 degree rotation of the curved needle about the axis along the first direction.

14. The method of claim 11, wherein the first input is received from a first input device and the second input is received from a second input device different from the first input device.

15. The method of claim 14, wherein:
the first input device comprises a first foot pedal and the second input device comprises a second foot pedal; or
the first input device comprises a first digital button and the second input device comprises a second digital button.

16. The method of claim 11, wherein the first input and the second input are each received from a same input device.

17. A non-transitory machine-readable medium comprising a plurality of machine-readable instructions which when executed by one or more processors are adapted to cause the one or more processors to perform a method comprising:
in response to receiving a first input, causing a drive mechanism of an end effector of a computer-assisted device to rotationally actuate a curved needle coupled to the drive mechanism by a first preset rotation amount along an arcuate path; and
in response to receiving a second input, causing the drive mechanism to rotationally actuate the curved needle by a second preset rotation amount along the arcuate path,
wherein the second preset rotation amount differs from the first preset rotation amount.

18. The non-transitory machine-readable medium of claim 17, wherein the arcuate path comprises a circular path and the drive mechanism is configured to rotationally actuate the curved needle about an axis that includes a center point of the circular path.

19. The non-transitory machine-readable medium of claim 18, wherein:
the first preset rotation amount is a 180 degree rotation of the curved needle about the axis along a first direction; and
the second preset rotation amount is a 360 degree rotation of the curved needle about the axis along the first direction.

20. The non-transitory machine-readable medium of claim 17, wherein the first input is received from a first input device and the second input is received from a second input device different from the first input device.

\* \* \* \* \*